(12) United States Patent
Watterson et al.

(10) Patent No.: US 6,227,797 B1
(45) Date of Patent: May 8, 2001

(54) ROTARY PUMP WITH HYDRODYNAMICALLY SUSPENDED IMPELLER

(75) Inventors: Peter Andrew Watterson, West Ryde; Geoffrey Douglas Tansley, Normanhurst; John Campbell Woodard, Thornleigh, all of (AU)

(73) Assignee: VentrAssist Pty Ltd and University of Technology, Sydney (AU)

( * ) Notice: Subject to any disclaimer, the term of this patent is extended or adjusted under 35 U.S.C. 154(b) by 0 days.

(21) Appl. No.: 09/281,608

(22) Filed: Mar. 30, 1999

Related U.S. Application Data

(63) Continuation of application No. PCT/AU98/00725, filed on Sep. 18, 1998.

(51) Int. Cl.[7] ............................... F01D 3/00; B63H 1/26
(52) U.S. Cl. .................... 415/107; 415/900; 415/228; 416/3; 416/228
(58) Field of Search ........................... 415/107, 206, 415/220, 227, 228, 900; 416/3, 223 R, 228, 234; 417/420

(56) References Cited

U.S. PATENT DOCUMENTS

| | | | |
|---|---|---|---|
| 4,382,199 | | 5/1983 | Isaacson . |
| 4,688,998 | * | 8/1987 | Olsen et al. ........................ 417/356 |
| 4,944,748 | | 7/1990 | Bramm et al. . |
| 5,055,005 | * | 10/1991 | Kletschka ...................... 415/900 X |
| 5,195,877 | * | 3/1993 | Kletschka ...................... 415/900 X |
| 5,322,413 | * | 6/1994 | Vescovini et al. ............. 415/206 X |
| 5,324,177 | * | 6/1994 | Golding et al. ................ 415/900 X |
| 5,326,344 | * | 7/1994 | Bramm et al. .................. 417/356 X |
| 5,470,208 | * | 11/1995 | Kletschka ...................... 415/900 X |
| 5,685,700 | * | 11/1997 | Izraelev ......................... 415/900 X |
| 5,800,559 | * | 9/1998 | Higham et al. ..................... 623/23 |
| 5,924,848 | * | 7/1999 | Izraelev ............................. 417/420 |
| 5,938,412 | * | 8/1999 | Izraelev ......................... 415/206 X |
| 5,947,892 | * | 9/1999 | Benkowski et al. ............ 415/900 X |
| 6,015,272 | * | 1/2000 | Antaki et al. .................. 415/900 X |
| 6,042,347 | * | 3/2000 | Scholl et al. .................. 417/423.12 |

FOREIGN PATENT DOCUMENTS

| | | |
|---|---|---|
| WO91/19103 | 12/1991 | (WO) . |
| WO94/13955 | 6/1994 | (WO) . |

\* cited by examiner

*Primary Examiner*—John E. Ryznic
(74) *Attorney, Agent, or Firm*—Knobbe, Martens, Olson & Bear, LLP

(57) ABSTRACT

This invention relates to rotary pumps adapted, but not exclusively, for use as artificial hearts or ventricular assist devices and, in particular, discloses in preferred forms a seal-less shaft-less pump featuring open or closed (shrouded) impeller blades with the edges of the blades used as hydrodynamic thrust bearing and with electromagnetic torque provided by the interaction between magnets embedded in the blades and a rotating current pattern generated in coils fixed relative to the pump housing.

26 Claims, 19 Drawing Sheets

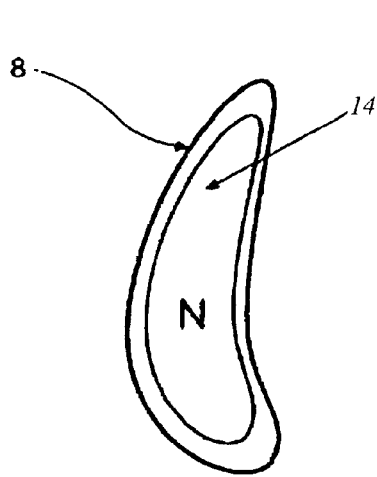
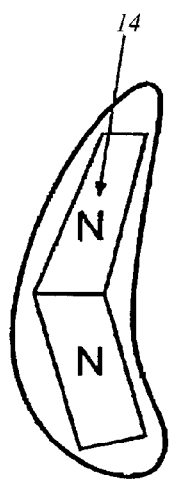
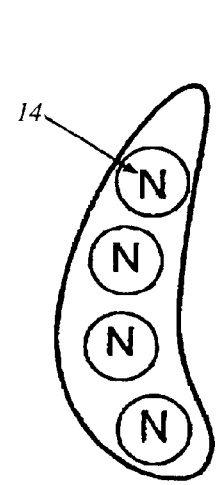
*FIG. 4A*  *FIG. 4B*  *FIG. 4C*

ROTARY PUMP WITH HYDRODYNAMICALLY SUSPENDED IMPELLER

This is a continuation application of PCT Application No. PCT/AU98/00725 filed Sep. 18, 1998.

FIELD OF THE INVENTION

This invention relates to rotary pumps adapted, but not exclusively, for use as artificial hearts or ventricular assist devices and, in particular, discloses in preferred forms a seal-less shaft-less pump featuring open or closed (shrouded) impeller blades with the edges of the blades used as hydrodynamic thrust bearings and with electromagnetic torque provided by the interaction between magnets embedded in the blades and a rotating current pattern generated in coils fixed relative to the pump housing.

BACKGROUND ART

This invention relates to the art of continuous or pulsatile flow rotary pumps and, in particular, to electrically driven pumps suitable for use although not exclusively as an artificial heart or ventricular assist device. For permanent implantation in a human patient, such pumps should ideally have the following characteristics: no leakage of fluids into or from the bloodstream; parts exposed to minimal or no wear; minimum residence time of blood in pump to avoid thrombosis (clotting); minimum shear stress on blood to avoid blood cell damage such as haemolysis; maximum efficiency to maximise battery duration and minimise blood heating; and absolute reliability.

Several of these characteristics are very difficult to meet in a conventional pump configuration including a seal, i.e. with an impeller mounted on a shaft which penetrates a wall of the pumping cavity, as exemplified by the blood pumps referred to in U.S. Pat. No. 3,957,389 to Rafferty et al., U.S. Pat. No. 4,625,712 to Wampler, and U.S. Pat. No. 5,275,580 to Yamazaki. Two main disadvantages of such pumps are firstly that the seal needed on the shaft may leak, especially after wear, and secondly that the rotor of the motor providing the shaft torque remains to be supported, with mechanical bearings such as ball-bearings precluded due to wear. Some designs, such as U.S. Pat. No. 4,625,712 to Wampler and U.S. Pat. No. 4,908,012 to Moise et al., have overcome these problems simultaneously by combining the seal and the bearing into one hydrodynamic bearing, but in order to prevent long residence times they have had to introduce means to continuously supply a blood-compatible bearing purge fluid via a percutaneous tube.

In seal-less designs, blood is permitted to flow through the gap in the motor, which is usually of the brushless DC type, i.e. comprising a rotor including permanent magnets and a stator in which an electric current pattern is made to rotate synchronously with the rotor. Such designs can be classified according to the means by which the rotor is suspended: contact bearings, magnetic bearings or hydrodynamic bearings, though some designs use two of these means.

Contact or pivot bearings, as exemplified by U.S. Pat. No. 5527159 to Bozeman et al. and U.S. Pat. No. 5,399,074 to Nose et al., have potential problems due to wear, and cause very high localised heating and shearing of the blood, which can cause deposition and denaturation of plasma proteins, with the risk of embolisation and bearing seizure.

Magnetic bearings, as exemplified by U.S. Pat. No. 5,350,283 to Nakazeki et al., U.S. Pat. No. 5,326,344 to Bramm et al. and U.S. Pat. No. 4,779,614 to Moise et al., offer contactless suspension, but require rotor position measurement and active control of electric current for stabilisation of the position in at least one direction, according to Earnshaw's theorem. Position measurement and feedback control introduce significant complexity, increasing the failure risk. Power use by the control current implies reduced overall efficiency. Furthermore, size, mass, component count and cost are all increased.

U.S. Pat. No. 5,507,629 to Jarvik claims to have found a configuration circumventing Earnshaw's Theorem and thus requiring only passive magnetic bearings, but this is doubtful and contact axial bearings are included in any case. Similarly, passive radial magnetic bearings and a pivot point are employed in U.S. Pat. No. 5,443,503 to Yamane.

Prior to the present invention, pumps employing hydrodynamic suspension, such as U.S. Pat. No. 5,211,546 to Isaacson et al. and U.S. Pat. No. 5,324,177 to Golding et al., have used journal bearings, in which radial suspension is provided by the fluid motion between two cylinders in relative rotation, an inner cylinder lying within and slightly off axis to a slightly larger diameter outer cylinder. Axial suspension is provided magnetically in U.S. Pat. No. 5,324,177 and by either a contact bearing or a hydrodynamic thrust bearing in U.S. Pat. No. 5,211,546.

A purging flow is needed through the journal bearing, a high shear region, in order to remove dissipated heat and to prevent long fluid residence time. It would be inefficient to pass all the fluid through the bearing gap, of small cross-sectional area, as this would demand an excessive pressure drop across the bearing. Instead a leakage path is generally provided from the high pressure pump outlet, through the bearings and back to the low pressure pump inlet, implying a small reduction in outflow and pumping efficiency. U.S. Pat. No. 5,324,177 provides a combination of additional means to increase the purge flow, namely helical grooves in one of the bearing surfaces, and a small additional set of impellers.

U.S. Pat. No. 5,211,546 provides 10 embodiments with various locations of cylindrical bearing surfaces. One of these embodiments, the third, features a single journal bearing and a contact axial bearing.

Embodiments of the present invention offer a relatively low cost and/or relatively low complexity means of suspending the rotor of a seal-less blood pump, thereby overcoming or ameliorating the problems of existing devices mentioned above.

SUMMARY OF THE INVENTION

According to one aspect of the present invention, there is disclosed a rotary blood pump with impeller suspended hydrodynamically by thrust forces generated on the edges of the impeller blades. The blade edges are shaped such that the gap between the edges and the housing at the leading edge is greater than at the trailing edge and thus the fluid which is drawn through the gap experiences a wedge shaped restriction which generates a thrust away from the housing, as described in Reynold's theory of lubrication.

In preferred embodiments of the invention, the pump is of centrifugal or mixed flow type with impeller blades open on both the front and back faces of the housing. At least one face of the housing is made conical, in order that the thrust perpendicular to it has a radial component, which provides a radial restoring force to a radial displacement of the impeller axis. Similarly, an axial displacement toward either the front or the back face increases the thrust from that face and reduces the thrust from the other face. Thus the sum of the forces on the impeller due to inertia (within limits), gravity and any bulk radial or axial hydrodynamic force on the impeller can be countered by a restoring force from the thrust bearings after a small displacement of the impeller within the housing relative to the housing in either a radial or axial direction.

In the preferred embodiment, the impeller driving torque derives from the magnetic interaction between permanent magnets within the blades of the impeller and oscillating currents in windings encapsulated in the pump housing.

In a second embodiment of the invention, the principle is applied in a pump of axial type. Within a uniform cylindrical section of the pump housing, tapered blade edges form a radial hydrodynamic bearing. If the pump housing is made with reducing radius at the two ends, then the end hydrodynamic thrust forces have an axial component which can provide the axial bearing. Alternatively, magnetic forces or other means can provide the axial bearing.

In a further broad form of the invention there is provided a rotary blood pump having an impeller suspended hydrodynamically by thrust forces generated by the impeller during movement in use of the impeller.

Preferably said thrust forces are generated by blades of said impeller or by deformities therein.

More preferably said thrust forces are generated by edges of said blades of said impeller.

Preferably said edges of said blades are tapered.

In an alternative preferred form said pump is of axial type.

Preferably within a uniform cylindrical section of the pump housing, tapered blade edges form a radial hydrodynamic bearing.

Preferably the pump housing is made with reducing radius at the two ends, and wherein the end hydrodynamic thrust forces have an axial component which can provide the axial bearing.

Preferably or alternatively magnetic forces or other means can provide the axial bearing.

In a further broad form of the invention there is provided a rotary blood pump having a housing within which an impeller acts by rotation about an axis to cause a pressure differential between an inlet side of a housing of said pump and an outlet side of the housing of said pump; said impeller suspended hydrodynamically by thrust forces generated by the impeller during movement in use of the impeller.

BRIEF DESCRIPTION OF THE DRAWINGS

Embodiments of the present invention will now be described, with reference to the accompanying drawings, wherein:

FIGS. 4A, 4B and 4C illustrate various possible locations of magnet material within a blade;

DETAILED DESCRIPTION OF PREFERRED EMBODIMENTS

The pump assemblies according to various preferred embodiments to be described below all have particular, although not exclusive, application for implantation in a mammalian body so as to at least assist, if not take over, the function of the mammalian heart. In practice this is performed by placing the pump assembly entirely within the body of the mammal and connecting the pump between the left ventricle and the aorta so as to assist left side heart function. It may also be connected to the right ventricle and pulmonary artery to assist the right side of the heart.

In this instance the pump assembly includes an impeller which is fully sealed within the pump body and so does not require a shaft extending through the pump body to support it. The impeller is suspended, in use, within the pump body by, at least, the operation of hydrodynamic forces imparted as a result of the interaction between the rotating impeller, the internal pump walls and the fluid which the impeller causes to be urged from an inlet of the pump assembly to an outlet thereof.

Figure 1:
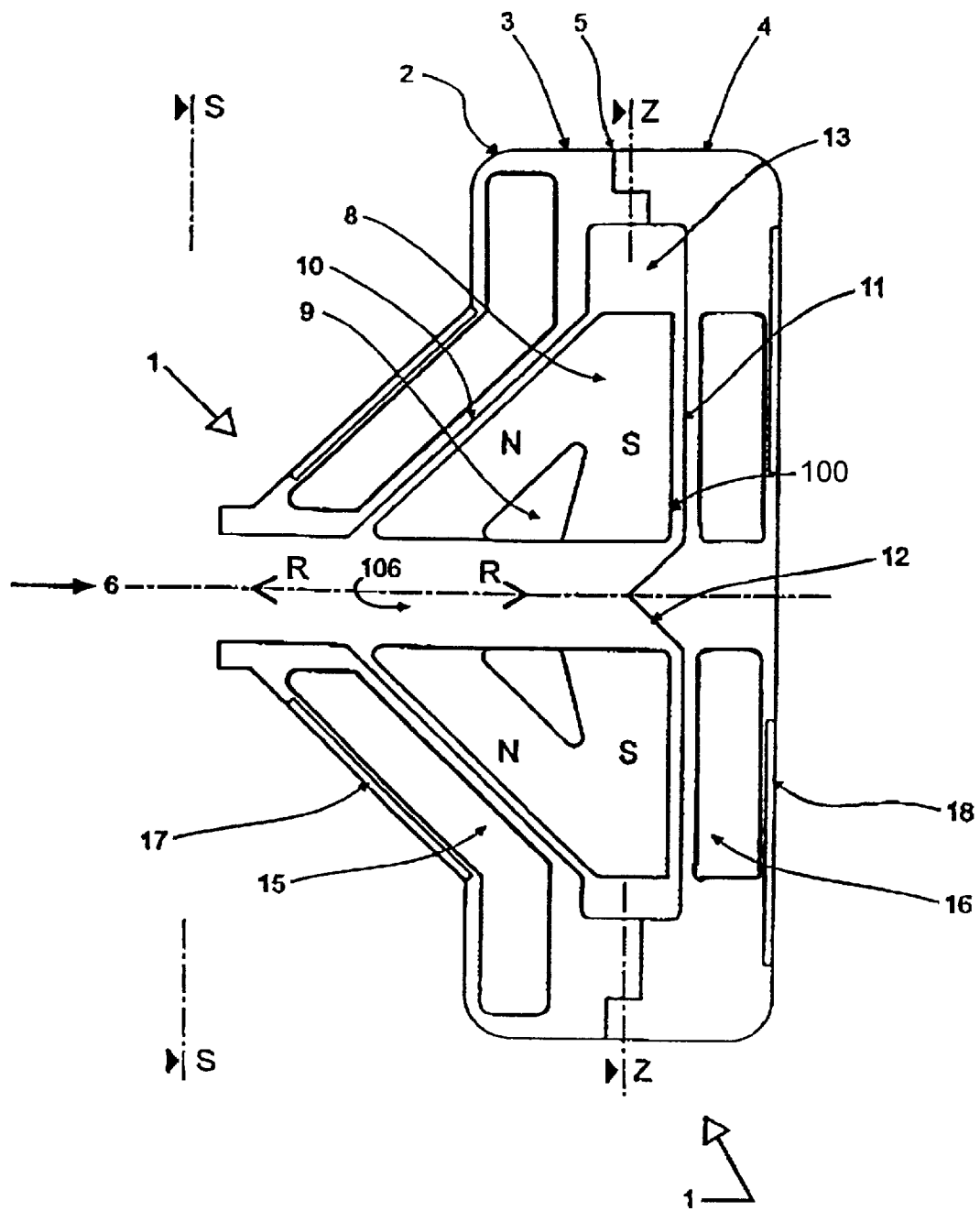
FIG. 1 is a longitudinal cross-sectional view of a preferred embodiment of the invention.
Figure 2:
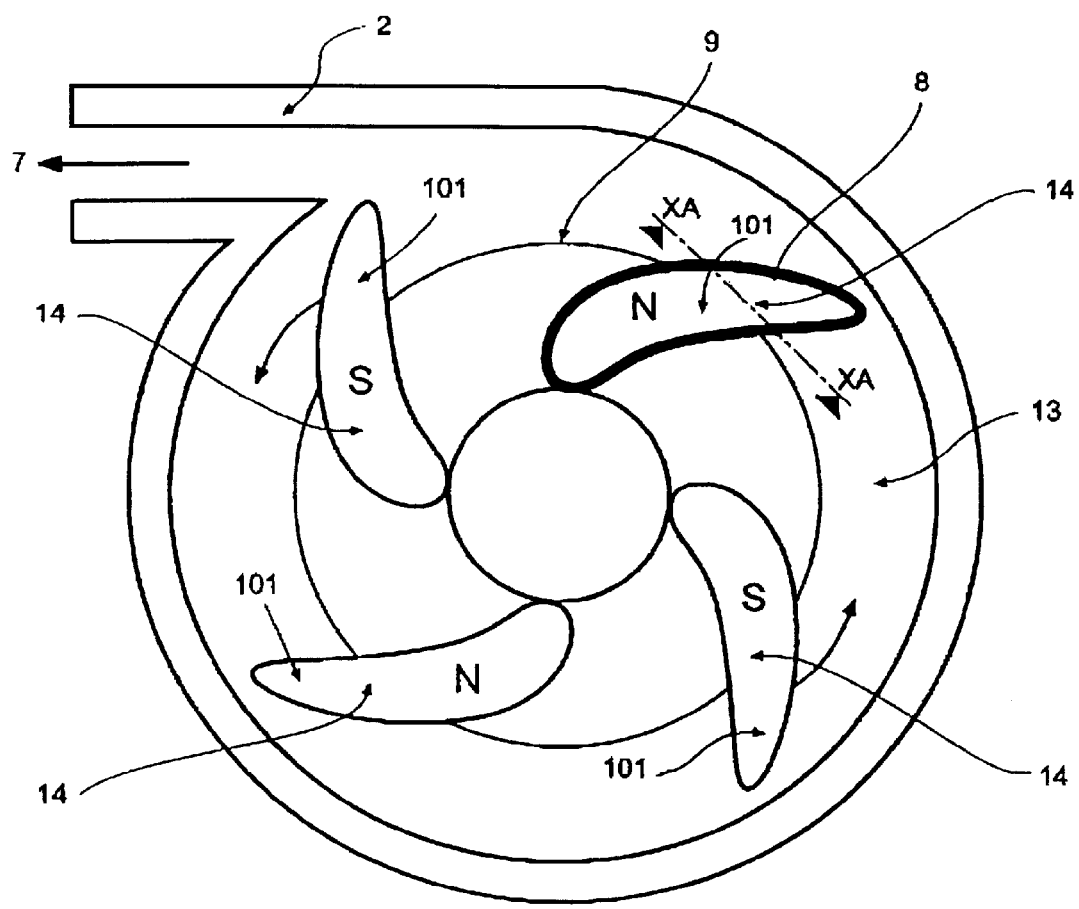
FIG. 2 is a cross-sectional view taken generally along the line Z—Z of FIG. 1.

A preferred embodiment of the invention is the centrifugal pump 1, as depicted in FIGS. 1 and 2, intended for implantation into a human body, in which case the fluid referred to below is blood. The pump housing 2, can be fabricated in two parts, a front part 3 in the form of a housing body and a back part 4 in the form of a housing cover, with a smooth join therebetween, for example at 5 in FIG. 1. The pump 1 has an axial inlet 6 and a tangential outlet 7. The rotating part or impeller 100 is of very simple form, comprising only blades 8 and a blade support 9 to hold those blades fixed relative to each other. The blades may be curved as depicted in FIG. 2, or straight, in which case they can be either radial or tilted, i.e. at an angle to the radius. This rotating part 100 will hereafter be called the impeller 100, but it also serves as a bearing component and as the rotor of a motor configuration as to be further described below whereby a torque is applied by electromagnetic means to the impeller 100. Note that the impeller has no shaft and that the fluid enters the impeller from the region of its axis RR. Some of the fluid passes in front of the support cone 9 and some behind it, so that the pump 1 can be considered of two-sided open type, as compared to conventional open centrifugal pumps, which are only open on the front side. Approximate dimensions found adequate for the pump 1 to perform as a ventricular assist device, when operating at speeds in the range 2,000 rpm to 4,000 rpm, are outer blade diameter 40 mm, outer housing average diameter 60 mm, and housing axial length 40 mm.

Figure 3A:
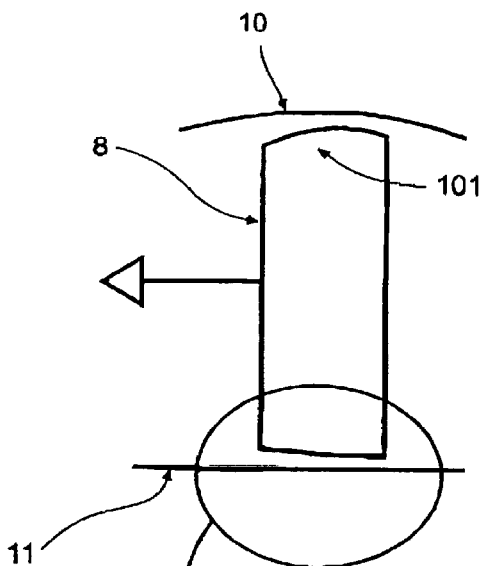
FIG. 3A is a cross-sectional view of an impeller blade taken generally along the line A—A of FIG. 2.
Figure 3C:
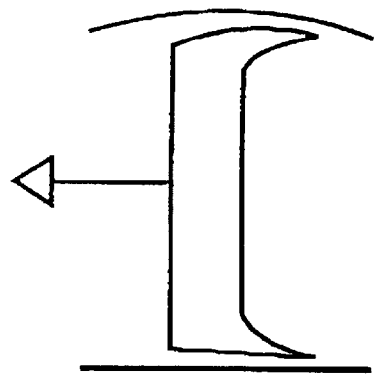
FIG. 3C is an alternative impeller blade shape.
Figure 3B:
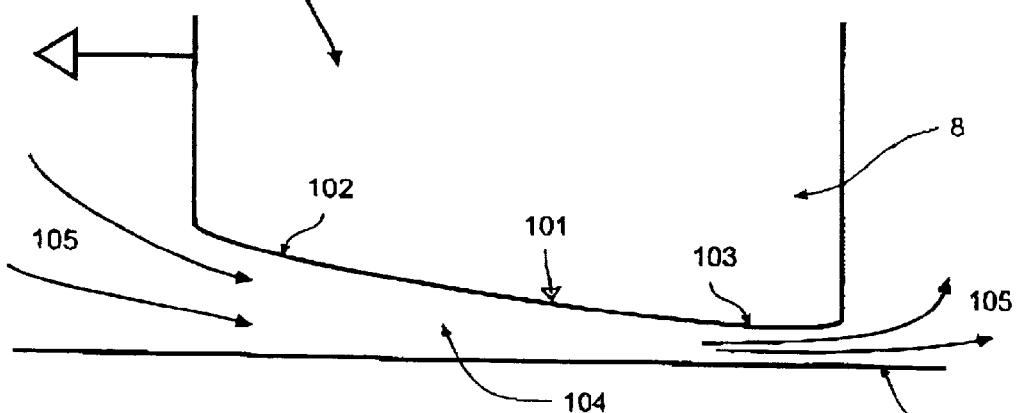
FIG. 3B is an enlargement of the blade-pump housing interface portion of FIG. 3A.

As the blades 8 move within the housing, some of the fluid passes through the gaps, much exaggerated in FIGS. 1 and 3, between the blade edges 101 and the housing front face 10 and housing back face 11. In all open centrifugal pumps, the gaps are made small because this leakage flow lowers the pump hydrodynamic efficiency. In the pump disclosed in this embodiment, the gaps are made slightly smaller than is conventional in order that the leakage flow can be utilised to create a hydrodynamic bearing. For the hydrodynamic forces to be sufficient, the blades must also be tapered as depicted in FIGS. 3A and 3B, so that the gap 104 is larger at the leading edge 102 of the blade 8 than at the trailing edge 103. The fluid 105 which passes through the gap thus experiences a wedge shaped restriction which generates a thrust, as described in Reynolds' theory of lubrication (see, for example, "Modern Fluid Dynamics, Vol. 1 Incompressible Flow", by N. Curle and H. J. Davies, Van Nostrand, 1968). The thrust is proportional to the square of the blade thickness at the edge, and thus thick blades are favoured, since if the proportion of the pump cavity filled by blades is constant, then the net thrust force will be inversely proportional to the number of blades. However, the blade edges can be made to extend as tails from thin blades as depicted in FIG. 3C in order to increase the blade area adjacent the walls.

In one particular form, the tails join adjacent blades so as to form a complete shroud with wedges or tapers incorporated therein. An example of a shroud design as well as other variations on the blade structure will be described later in this specification.

For manufacturing simplicity, the housing front face 10 can be made conical, with an angle of around 45º so that it provides both axial and radial hydrodynamic forces. Other angles are suitable that achieve the functional requirements of this pump including the requirements for both axial and radial hydrodynamic forces.

Other curved surfaces are possible provided both axial and radial hydrodynamic forces can be produced as a result of rotation of the blades relative to the housing surfaces.

The housing back face 11 can include a roughly conical extension 12 pointing into the pump cavity 106, to eliminate or minimise the effect of the flow stagnation point on the axis of the back housing.

Alternatively extension 12 can resemble an impeller eye to make the flow mixed.

In this preferred embodiment, for manufacturing simplicity and for uniformity in the flow axial direction RR, the housing back face 11 is made flat over the bearing surfaces, i.e. under the blade edges. With this the case, a slacker tolerance on the alignment between the axes of the front part 3 and back part 4 of the housing 2 is permissible. An alternative is to make the back face 11 conical at the bearing surfaces, with taper in the opposite direction to the front face 10, so that the hydrodynamic forces from the back face will also have radial components. Tighter tolerance on the axes alignment would then be required, and some of the flow would have to undergo a reversal in its axial direction. Again a roughly conical extension (like 12) will be needed. There may be some advantage in making the housing surfaces and blade edges non-straight, with varying tangent angle, although this will impose greater manufacturing complexity.

There are several options for the shape of the taper, but in the preferred embodiment the amount of material removed simply varies linearly or approximately linearly across the blade. For the back face, the resulting blade edges are then planes at a slight inclination to the back face. For the front face, the initial blade edges are curved and the taper only removes a relatively small amount of material so they still appear curved. Alternative taper shapes can include a step in the blade edge, though the corner in that step would represent a stagnation line posing a thrombosis risk.

For a given minimum gap, at the trailing blade edge, the hydrodynamic force is maximal if the gap at the leading edge is approximately double that at the trailing edge. Thus the taper, which equals the leading edge gap minus the trailing edge gap, should be chosen to match a nominal minimum gap, once the impeller has shifted towards that edge. Dimensions which have been found to give adequate thrust forces are a tape r of around 0.05 mm for a nominal minimum gap of around 0.05 mm, and an average circumferential blade edge thickness of around 5 mm for 4 blades. For the front face, the taper is measured within the plane perpendicular to the axis. The axial length of the housing between the front and back faces at any position should then be made about 0.2 mm greater than the axial length of the blade, when it is coaxial with the housing, so that the minimum gaps are both about 0.1 mm axially when the impeller 100 is centrally positioned within the housing 2. Then, for example, if the impeller shifts axially by 0.05 mm, the minimum gaps will be 0.05 mm at one face and 0.15 mm at the other face. The thrust increases with decreasing gap and would be much larger from the 0.05 mm gap than from the 0.15 mm gap, about 14 times larger for the above dimensions. Thus there is a net restoring force away from the smaller gap.

Similarly, for radial shifts of the impeller the radial component of the thrust from the smaller gap on the conical housing front face would offer the required restoring radial force. The axial component of that force and its torque on the impeller would have to be balanced by an axial force and torque from the housing back face, and so the impeller will also have to shift axially and tilt its axis to be no longer parallel with the housing axis. Thus as the person moves and the pump is accelerated by external forces, the impeller will continually shift its position and alignment, varying the gaps in such a way that the total force and torque on the impeller 100 match that demanded by inertia. The gaps are so small, however, that the variation in hydrodynamic efficiency will be small, and the pumping action of the blades will be approximately the same as when the impeller is centrally located.

While smaller gaps imply greater hydrodynamic efficiency and greater bearing thrust forces, smaller gaps also demand tighter manufacturing tolerances, increase frictional drag on the impeller, and impose greater shear stress an the fluid. Taking these points in turn, for the above 0.05 mm tapers and gaps, tolerances of around ±0.015 mm are needed, which imposes some cost penalty but is achievable. A tighter tolerance is difficult, especially if the housing is made of a plastic, given the changes in dimension caused by temperature and possible absorption of fluid by plastic. The frictional drag for the above gaps produces much smaller torque than the typical motor torque. Finally, to estimate the shear stress, consider a rotation speed of 3,000 rpm and a typical radius of 15 mm, at which the blade speed is 4.7 ms$^{-1}$ and the average velocity shear for an average gap of 0.075 mm is $6.2 \times 10^4$ s$^{-1}$. For blood of dynamic viscosity $3.5 \times 10^{-3}$ kgm$^{-1}$s$^{-1}$, the average shear stress would be 220 Nm$^{-2}$. Other prototype centrifugal blood pumps with closed blades have found that slightly larger gaps, e.g. 0.15 mm, are acceptable for haemolysis. A major advantage of the open blades of the present invention is that a fluid element that does pass through a blade edge gap will have very short residence time in that gap, around $2 \times 10^{-3}$ S, and the fluid element will most likely be swept though the pump without passing another blade edge.

To minimise the net force required of the hydrodynamic bearings, the net axial and radial hydrodynamic forces on the impeller from the bulk fluid flow should be minimised, where "bulk" here means other than from the bearing thrust surfaces.

One method of minimising the bulk radial hydrodynamic force is to use straight radial blades so that pressure acting on the blade sides has virtually no radial component. The radial force on the impeller depends critically on the shape of the output flow collector or volute 13. The shape should be designed to minimise the radial impeller force over the desired range of pump speeds, without excessively lowering the pump efficiency. The optimal shape will have a roughly helical perimeter between the "cut water" and outlet. The radial force can also be reduced by the introduction of an internal division in the volute 13 to create a second output flow collector passage, with tongue approximately diametrically opposite to the tongue of the first passage.

An indicative plan view of impeller 100 relative to housing 2 is shown in FIG. 2 having a concentric volute 13.

Figure 17:
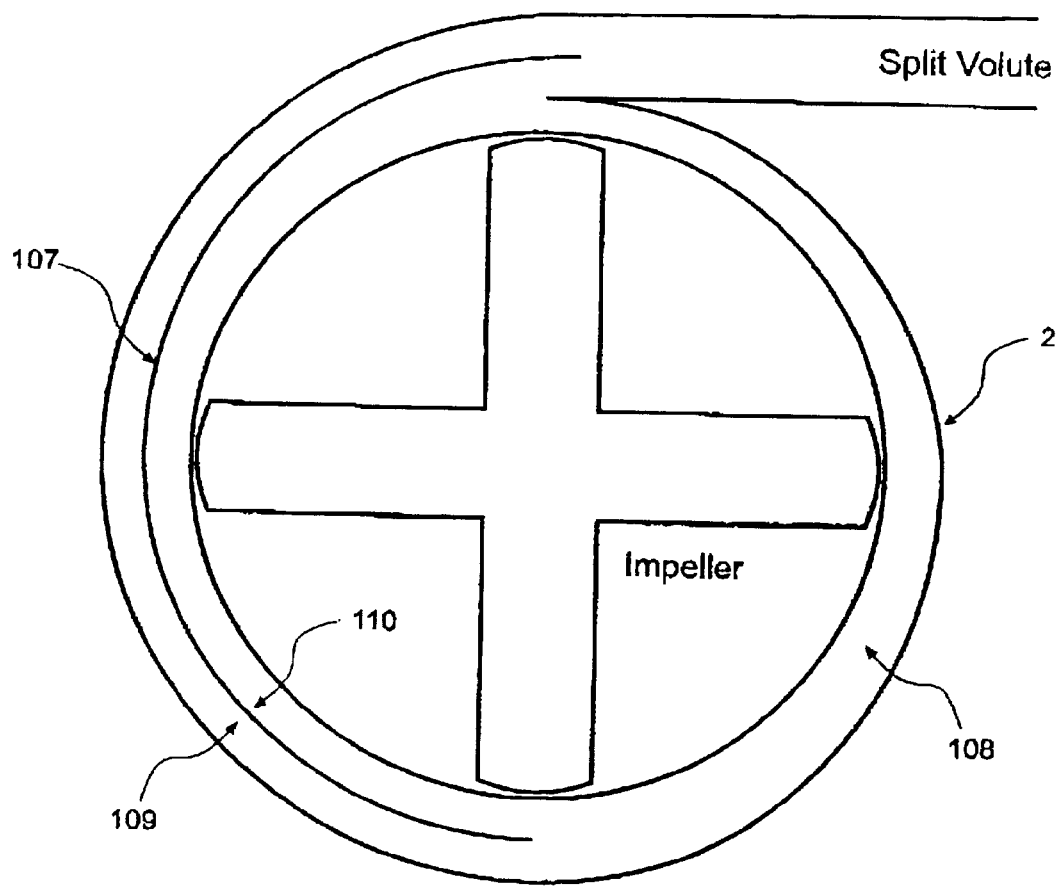
FIG. 17 is a plan, section view of a pump assembly showing an alternative volute arrangement.

FIG. 17 illustrates the alternative volute arrangement comprising a split volute created by volute barrier 107 which causes volute 108 in a first hemisphere of the housing 2 to split into first half volute 109 and second half volute 110 over the second hemisphere. The hemispheres are defined respectively on each side of a diameter of the housing 2 which passes through or near exit point 111 of outlet 7.

In alternative forms concentric volutes can be utilised, particularly where specific speed is relatively low.

In a further particular form a vaneless diffuser may also reduce the radial force.

In regard to the bulk axial hydrodynamic axial force, if the blade cross-section is made uniform in the axial direction along the relational axis, apart from the conical front edge, then the pressure acting on the blade surface (excluding the bearing edges) will have no axial component. This also simplifies the blade manufacture. The blade support cone 9 must then be shaped to minimise axial thrust on the impeller and minimise disturbance to the flow over the range of speeds, while maintaining sufficient strength to prevent relative blade movement. The key design parameter affecting the axial force is the angle of the cone. The cone is drawn in FIG. 1 as having the same internal diameter as the blades, which may aid manufacture. However, the cone could be made with larger or smaller internal diameter to the blades. There may be advantage in using a non-axisymmetric support "cone", e.g. with larger radius on the trailing surface of a blade than the radius at the leading surface of the next blade. If the blades are made with non-uniform cross-section to increase hydrodynamic efficiency, then any bulk hydrodynamic axial force on them can be balanced by shaping the support cone to produce an opposite bulk hydrodynamic axial force on it.

Careful design of the entire pump, employing computational fluid dynamics, is necessary to determine the optimal shapes of the blades 8, the volute 13, the support cone 9 and the housing 2, in order to maximise hydrodynamic efficiency while keeping the bulk fluid hydrodynamic forces, shear and residence times low. All edges and the joins between the blades and the support cone should be smoothed.

The means of providing the driving torque on the impeller 100 of the preferred embodiment of the invention is to encapsulate permanent magnets 14 in the blades 8 of the impeller 100 and to drive them with a rotating magnetic field pattern from oscillating currents in windings 15 and 16, fixed relative to the housing 2. Magnets of high remanence such as sintered rare-earth magnets should be used to maximise motor efficiency. The magnets should be aligned axially or approximately axially, with alternating polarity for adjacent blades. Thus there must be an even number of blades. Since low blade number is preferred for the bearing force, and since two blades would not have sufficient bearing stiffness to rotation about an axis through the blades and perpendicular to the pump housing (unless the blades are very curved), four blades are recommended. A higher number of blades, for example 6 or 8 will also work.

Some possible options for locating the magnets 14 within the blades 8 are shown in FIG. 4. The most preferred which is depicted in FIG. 4A, is for the blade to be made of magnet material apart from a biocompatible shell or coating to prevent fluid corroding the magnets and to prevent magnet material (which may be toxic) entering the blood stream. The coating should also be sufficiently durable especially at blade corners to withstand rubbing during start-up or during inadvertent bearing touch down.

In one particular form the inside walls of the pump housing 2 are also coated with a biologically compatible and wear resistant material such as diamond coating or titanium nitride so that wear on both of the touching surfaces is minimised.

An acceptable coating thickness is approximately 1 micron.

A suitable impeller manufacturing method is to die-press the entire impeller, blades and support cone, as a single axially aligned magnet. The die-pressing is much simplified if near axially uniform blades are used (blades with an overhang such as in FIG. 3C are precluded). During pressing, the crushed rare-earth particles must be aligned in an axial magnetic field. This method of die-pressing with parallel alignment direction is cheaper for rare-earth magnets, although it produces slightly lower remanence magnets. The tolerance in die-pressing is poor, and grinding of the tapered blade edges is required. Then the magnet impeller can be coated, for example by physical vapour deposition, of titanium nitride for example, or by chemical vapour deposition, of a thin diamond coating or a teflon coating.

In an alternative form the magnet material can be potted in titanium or a polymeric housing which is then, in turn, coated with a biologically compatible and tough material such as diamond coating or titanium nitride.

Finally, to create the alternating blade polarity the impeller must be placed in a special pulse magnetisation fixture, with an individual coil surrounding each blade. The support cone may acquire some magnetisation near the blades, with negligible influence.

Alternative magnet locations are sketched in FIG. 4B and FIG. 4C in which quadrilateral or circular cross-section magnets 14 are inserted into the blades. Sealing and smoothing of the blade edges over the insertion holes is then required to reinstate the taper.

All edges in the pump should be radiused and surfaces smoothed to avoid possible damage to formed elements of the blood.

The windings 15 and 16 of the preferred embodiment are slotless or air-gap windings, following the blade curvature, with the same pole number as the impeller, namely four poles in the preferred embodiment. A ferromagnetic iron yoke 17 of conical form for the front winding and an iron ferromagnetic yoke 18 of annular form for the back winding may be placed on the outside of the windings to increase the magnetic flux densities and hence increase motor efficiency. The winding thicknesses should be designed for maximum motor efficiency, with the sum of their axial thicknesses somewhat less than but comparable to the magnet axial length. The yokes can be made of solid ferromagnetic material such as iron. To reduce "iron" losses, the yokes 17 can be laminated, for example by helically winding thin strip, or can be made of iron/powder epoxy composite. Alternatively they can be helically wound to reduce iron losses. The yokes should be positioned such that there is zero net axial magnetic force on the impeller when it is positioned centrally in the housing. The magnetic force is unstable and increases linearly with axial displacement of the impeller away from the central position, with the gradient being called the positive stiffness of the magnetic force. This unstable magnetic force must be countered by the hydrodynamic bearings, and so the stiffness should be made as small as possible. Choosing the yoke thickness such that the flux density is at the saturation level reduces the stiffness and gives minimum mass. An alternative would be to have no iron yokes, completely eliminating the unstable axial magnetic force, but the efficiency of such designs would be lower and the magnetic flux density in the immediate vicinity of the pump may violate safety standards and produce some tissue heating. In any case, the stiffness is acceptably small for slotless windings with the yokes present. Another alternative would be to insert the windings in slots in laminated iron stators which would increase motor efficiency and enable use of less magnet material and potentially lighter impeller blades. However, the unstable magnetic forces would be significant for such slotted motors. Also, the necessity for fat blades to generate the required bearing forces allows room for large magnets, and so slotless windings are chosen in the preferred embodiment.

Figure 5:
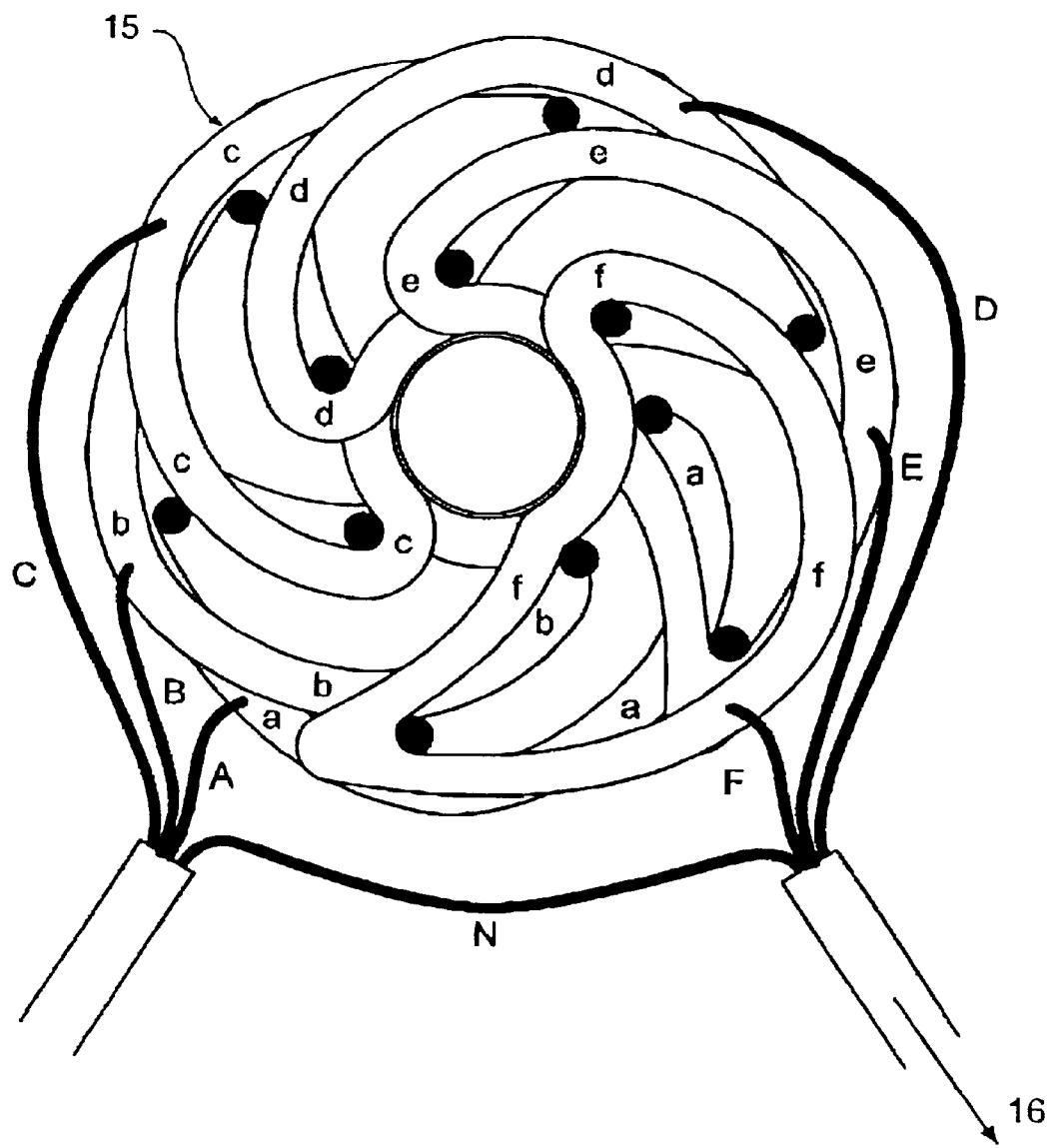
FIG. 5 is a left-hand end view of a possible winding geometry taken generally along the line S—S of FIG. 1.

FIG. 5 depicts one suitable topology for the front face winding 15. The back face winding 16 looks similar from the back end of the motor, except the hole on the axis is smaller. Each winding has three phases, A, B and C, and two coils connected in series or parallel per phase. Each coil comprises a number of turns of an insulated conductor such as copper, with the number of turns chosen to suit the desired voltage. The conductor may need to be stranded to reduce eddy losses. The winding construction can be simplified by laying the coils around pins protruding from a temporary conical former, the pins shown as dots in two rings of six pins each in FIG. 5. The coils are labelled alphabetically in the order in which they would be layed, coils a and d for phase A, b and e for phase B, and c and f for phase C. Instead of or as well as pins, the coil locations can be defined by thin curved fins, running between the pins in FIG. 5, along the boundary between the coils.

The winding connection of the preferred embodiment is for three wires, one wire per phase, to connect a sensorless electronic controller to winding 15, three wires to pass between windings 15 and 16, and for a neutral point termination of the wires within winding 16. A neutral lead, N in FIG. 5, between the controller and the neutral point is optional. A standard sensorless controller can be used, in which two out of six semiconducting switches in a three phase bridge are turned on at any one time, with the switching synchronised with the impeller position via the back-emf in the unenergised phase. Alternatively, because of the relatively small fraction of the impeller cross-section occupied by magnets, it may be slightly more efficient to only activate one of the three phases at a time, and to return the current by a fourth wire from the winding 16 neutral point back to the controller. The provision of the neutral lead also enables redundancy to be built into the motor and controller, so that if any one of the three phases fails in either the motor or controller, then the other two phases can still provide a rotating magnetic field sufficient to drive the pump. Careful attention must be paid to ensure that the integrity of all leads and connections is failsafe.

In the preferred embodiment, the two housing components 3 and 4 are made by injection moulding from non-conducting plastic materials such as Lexan polycarbonate plastic or ceramics. The windings and yokes are encapsulated within the housing during fabrication moulding. In this way, the separation between the winding and the magnets is minimised, increasing the motor efficiency, and the housing is thick, increasing its mechanical stiffness. Alternatively, the windings can be positioned outside the housing, of thickness at least around 2 mm for sufficient stiffness.

If the housing material plastic is hygroscopic or if the windings are outside the housing, it may be necessary to first enclose the windings and yoke in a very thin impermeable shell. Ideally the shell should be non-conducting (such as ceramic or plastic), but titanium of around 0.1 mm to 0.2 mm thickness would give sufficiently low eddy losses. Encapsulation within such a shell would be needed to prevent winding movement.

By keeping the windings separate for the front and back faces, the windings can be moulded into the front and back housing parts. Alternatively, for the case of windings not moulded into the housings, it may be possible to wind the coils onto the assembled housing, passing the coils from the front face to the back face over the volute 13.

The combining of the motor and bearing components into the impeller in the preferred embodiment provides several key advantages. The rotor consequently has very simple form, with the only cost of the bearing being tight manufacturing tolerances. The rotor mass is very low, minimising the bearing force needed to overcome weight. Also, with the bearings and the motor in the same region of the rotor, the bearings forces are smaller than if they had to provide a torque to support magnets at an extremity of the rotor.

A disadvantage of the combination of functions in the impeller is that its design is a coupled problem. The optimisation should ideally link the fluid dynamics, magnetics and bearing thrust calculations. In reality, the blade thickness can be first roughly sized to give adequate motor efficiency and sufficient bearing forces with a safety margin. Fortuitously, both requirements are met for four blades of approximate average circumferential thickness 5 mm. The housing, blade, and support cone shapes can then be designed using computational fluid dynamics, maintaining the above minimum average blade thickness. Finally the motor stator, i.e. winding and yoke, can be optimised for maximum motor efficiency.

Figure 6:
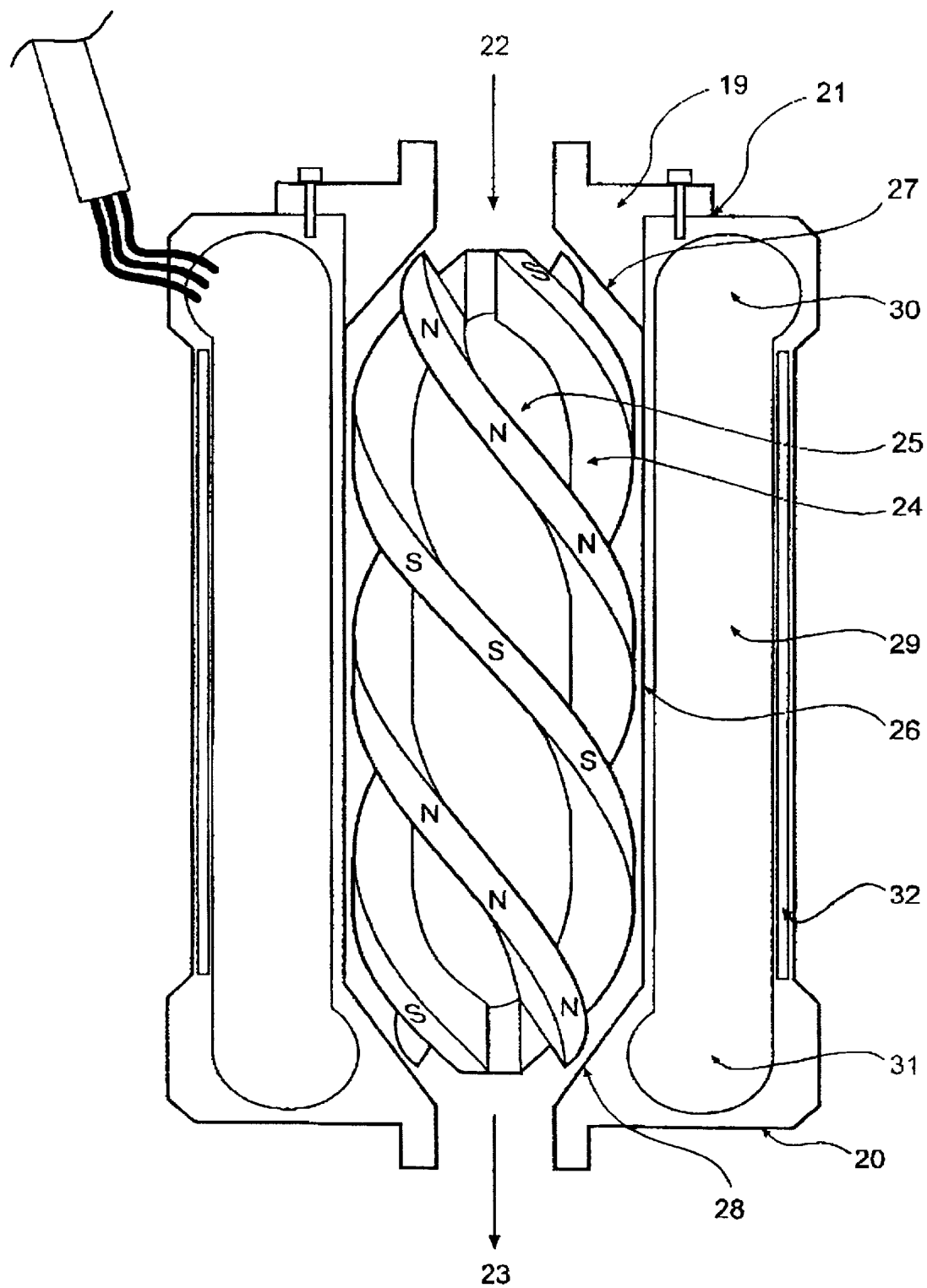
FIG. 6 is a diagrammatic cross-sectional view of an alternative embodiment of the invention as an axial pump.

FIG. 6 depicts an alternative embodiment of the invention as an axial pump. The pump housing is made of two parts, a front part 19 and a back part 20, joined for example at 21. The pump has an axial inlet 22 and axial outlet 23. The impeller comprises only blades 24 mounted on a support cylinder 25 of reducing radius at each end. An important feature of this embodiment is that the blade edges are tapered to generate hydrodynamic thrust forces which suspend the impeller. These forces could be used for radial suspension alone from the straight section 26 of the housing, with some alternative means used for axial suspension, such as stable axial magnetic forces or a conventional tapered-land type hydrodynamic thrust bearing. FIG. 6 proposes a design which uses the tapered blade edges to also provide an axial hydrodynamic bearing. The housing is made with a reducing radius at its ends to form a front face 27 and a back face 28 from which the axial thrusts can suspend the motor axially. Magnets are embedded in the blades with blades having alternating polarity and four blades being recommended. Iron in the outer radius of the support cylinder 25 can be used to increase the magnet flux density. Alternatively, the magnets could be housed in the support cylinder and iron could be used in the blades. A slotless helical winding 29 is recommended, with outward bending end-windings 30 at one end to enable insertion of the impeller and inward bending windings 31 at the other end to enable insertion of the winding into a cylindrical magnetic yoke 32. The winding can be encapsulated in the back housing part 20.

THIRD EMBODIMENT

With reference to FIGS. 7 to 15 inclusive there is shown a further preferred embodiment of the pump assembly 200.

Figure 7:
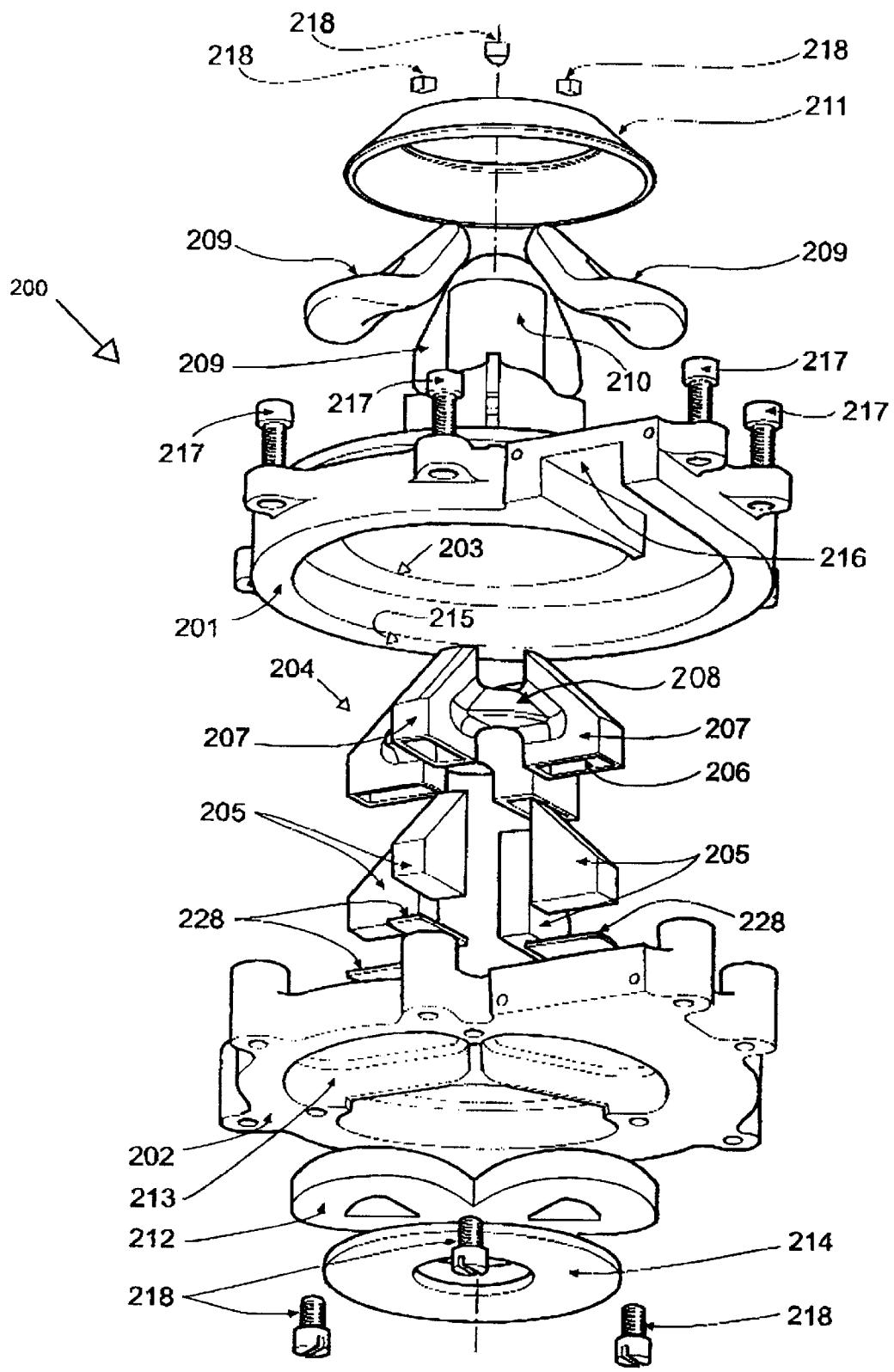
FIG. 7 is an exploded, perspective view of a centrifugal pump assembly according to a further embodiment of the invention.

With particular reference initially to FIG. 7 the pump assembly 200 comprises a housing body 201 adapted for bolted connection to a housing cover 202 and so as to define a centrifugal pump cavity 203 therewithin.

The cavity 203 houses an impeller 204 adapted to receive magnets 205 within cavities 206 defined within blades 207. As for the first embodiment the blades 207 are supported from a support cone 208.

Exterior to the cavity 203 but forming part of the pump assembly 200 there is located a body winding 209 symmetrically mounted around inlet 210 and housed between the housing body 201 and a body yoke 211.

Also forming part of the pump assembly 200 and also mounted external to pump cavity 203 is cover winding 212 located within winding cavity 213 which, in turn, is located within housing cover 202 and closed by cover yoke 214.

Figure 12:
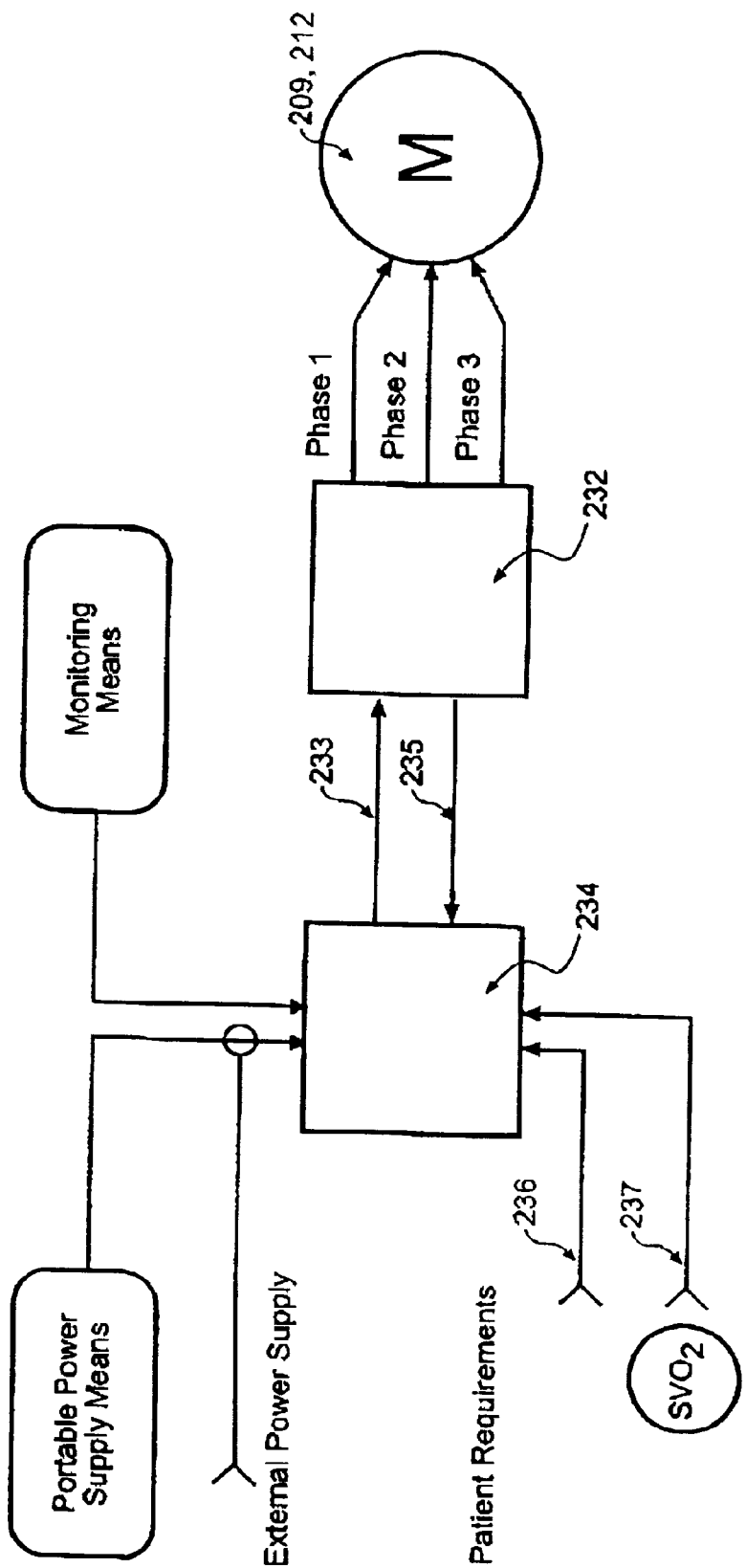
FIG. 12 is a block diagram of an electronic driver circuit for the pump assembly of FIG. 7.

The windings 212 and 209 are supplied from the electronic controller of FIG. 12. As for the first embodiment the windings are arranged to receive a three phase electrical supply and so as to set up a rotating electrical field within cavity 203 which exerts a torque on magnets 205 within the impeller 204 so as to urge the impeller 204 to rotate substantially about central axis TT of cavity 203 and in line with the longitudinal axis of inlet 210. The impeller 204 is caused to rotate so as to urge fluid (in this case blood liquid) around volute 215 and through outlet 216.

The assembly is bolted together in the manner indicated by screws 217. The yokes 211, 214 are held in place by fasteners 218. Alternatively, press fitting is possible provided sufficient integrity of seal can be maintained.

Figure 8:
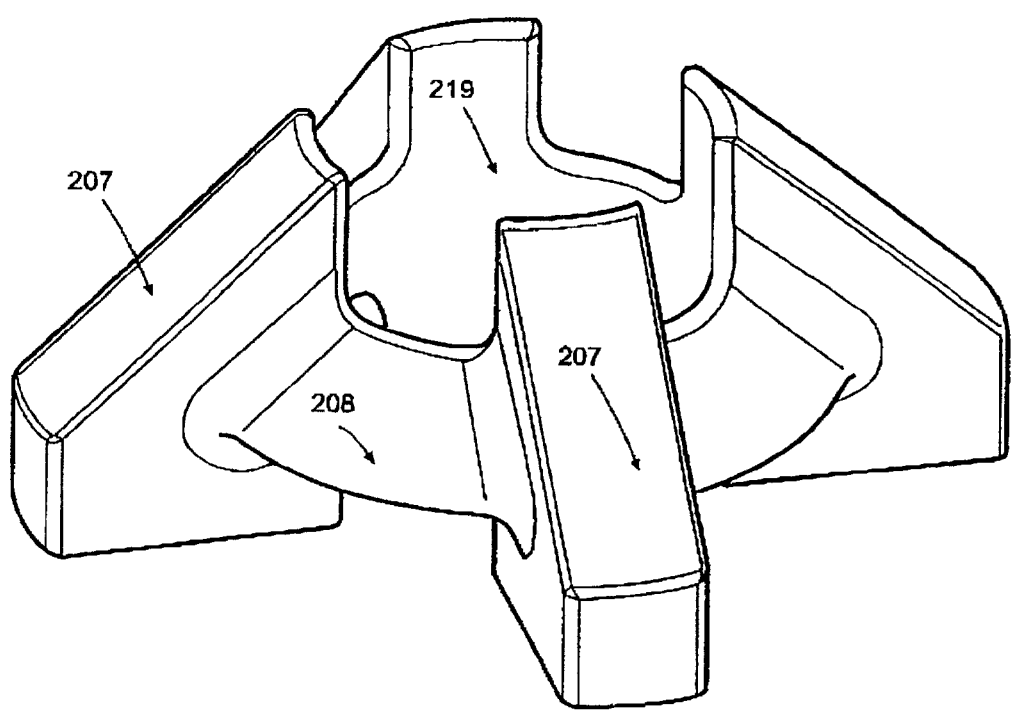
FIG. 8 is a perspective view of the impeller of the assembly of FIG. 7.

FIG. 8 shows the impeller 204 of this embodiment and clearly shows the support cone 208 from which the blades 207 extend. The axial cavity 219 which is arranged, in use, to be aligned with the longitudinal axis of inlet 210 and through which blood is received for urging by blades 207 is clearly visible.

Figure 9:
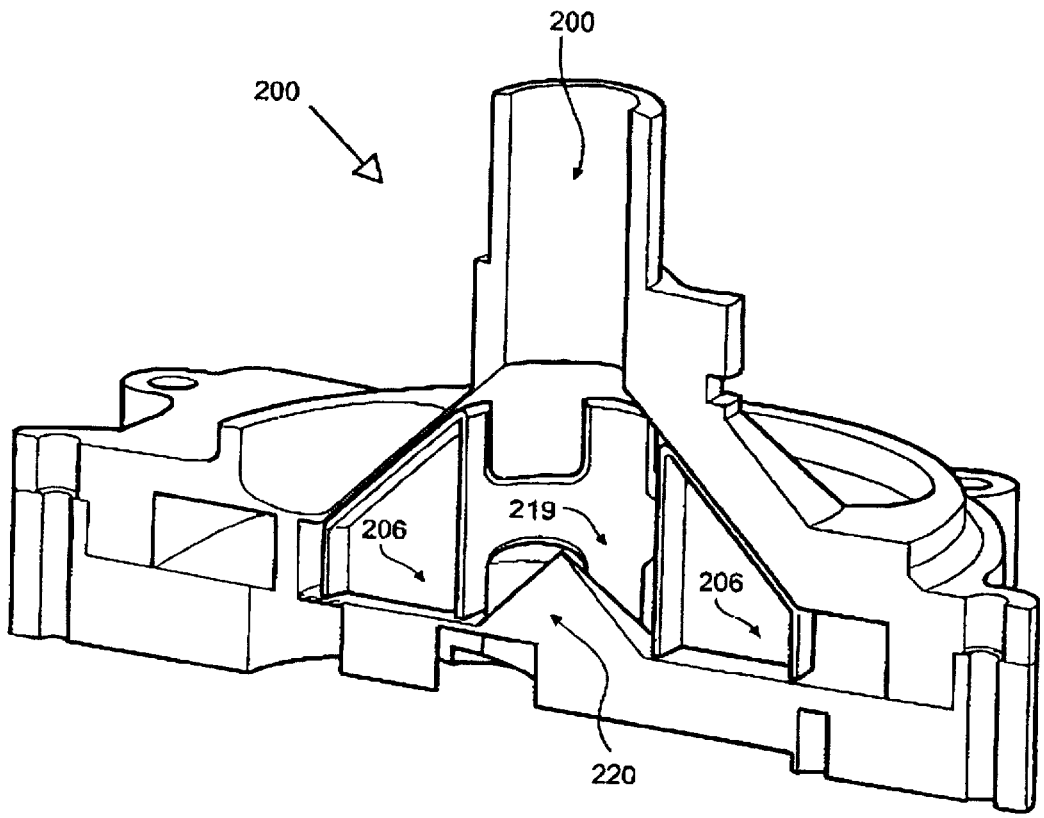
FIG. 9 is a perspective, cut away view of the impeller of FIG. 8 within the pump assembly of FIG. 7.

The cutaway view of FIG. 9 shows the axial cavity 219 and also the magnet cavities 206 located within each blade 207. The preferred cone structure 220 extending from housing cover 202 aligned with the axis of inlet 210 and axial cavity 219 of impeller 204 is also shown.

Figure 10:
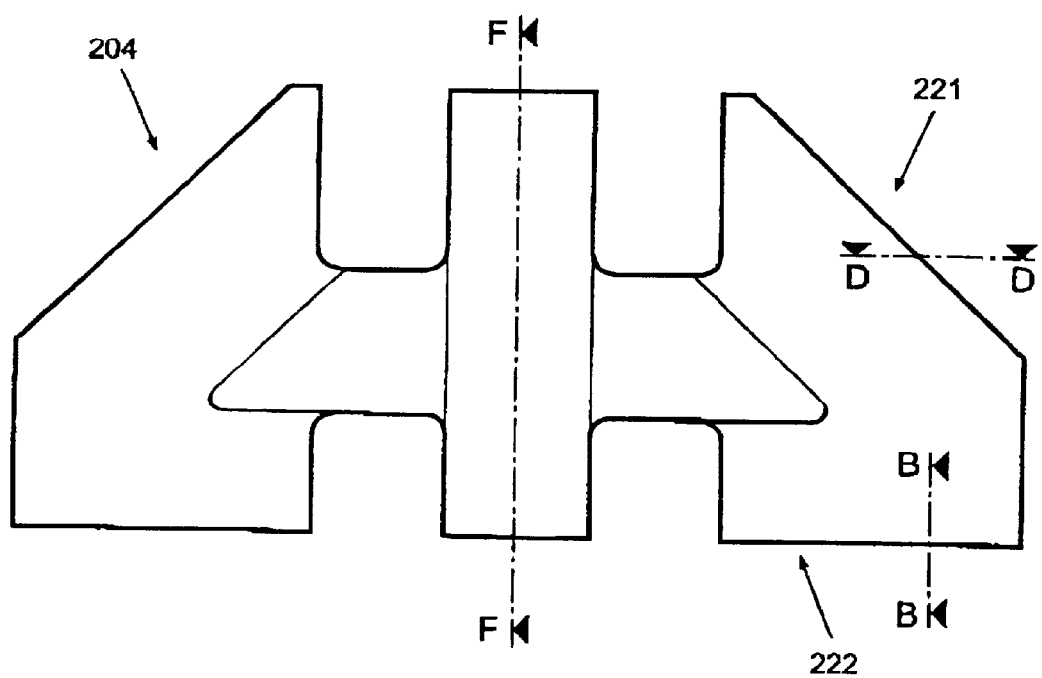
FIG. 10 is a side section indicative view of the impeller of FIG. 8.

FIG. 10 is a side section, indicative view of the impeller 204 defining the orientations of central axis FF, top taper edge DD and bottom taper edge BB, which tapers are illustrated in FIG. 11 in side section view.

Figure 11A:
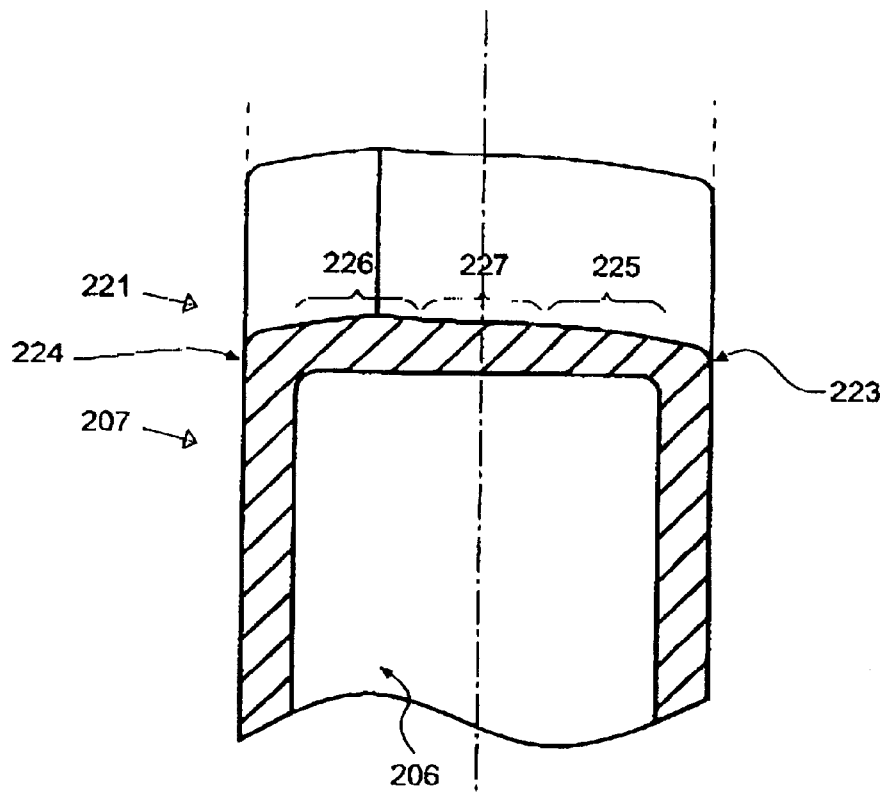
FIG. 11 is a detailed view in side section of edge portions of the impeller of FIG. 10.

FIG. 11A is a section of a blade 207 of impeller 204 taken through plane DD as defined in FIG. 10 and shows the top edge 221 to be profiled from a leading edge 223 to a trailing edge 224 as follows: central portion 227 comprises an ellipse having a semi-major axis of radius 113 mm and a semi-minor axis of radius 80 mm subtended on either side by a region of no radius and then followed by leading conical surface 225 and trailing conical surface 226 on either side thereof as illustrated in FIG. 11A.

The leading edge 223 is radiused as illustrated.

Figure 11B:
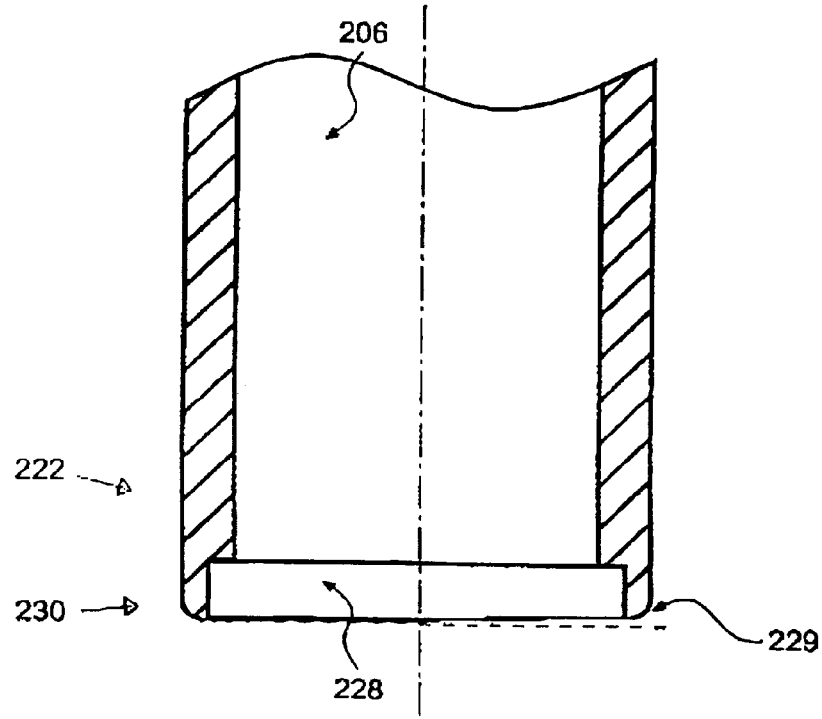

FIG. 11B illustrates in cross-section the bottom edge 222 of blade 207 cut along plane BB of FIG. 10.

The bottom edge includes cap 228 utilised for sealing magnet 205 within cavity 206.

In this instance substantially the entire edge comprises a straight taper with a radius of 0.05 mm at leading edge 229 and a radius of 0.25 mm at trailing edge 230.

The blade 207 is 5.4 mm in width excluding the radii at either end.

FIG. 12 comprises a block diagram of the electrical controller suitable for driving the pump assembly 200 and comprises a three phase commutation controller 232 adapted to drive the windings 209, 212 of the pump assembly. The commutation controller 232 determines relative phase and frequency values for driving the windings with reference to set point speed input 233 derived from physiological controller 234 which, in turn, receives control inputs 235 comprising motor current input and motor speed (derived from the commutation controller 232), patient blood flow 236, and venous oxygen saturation 237.

Figure 13:
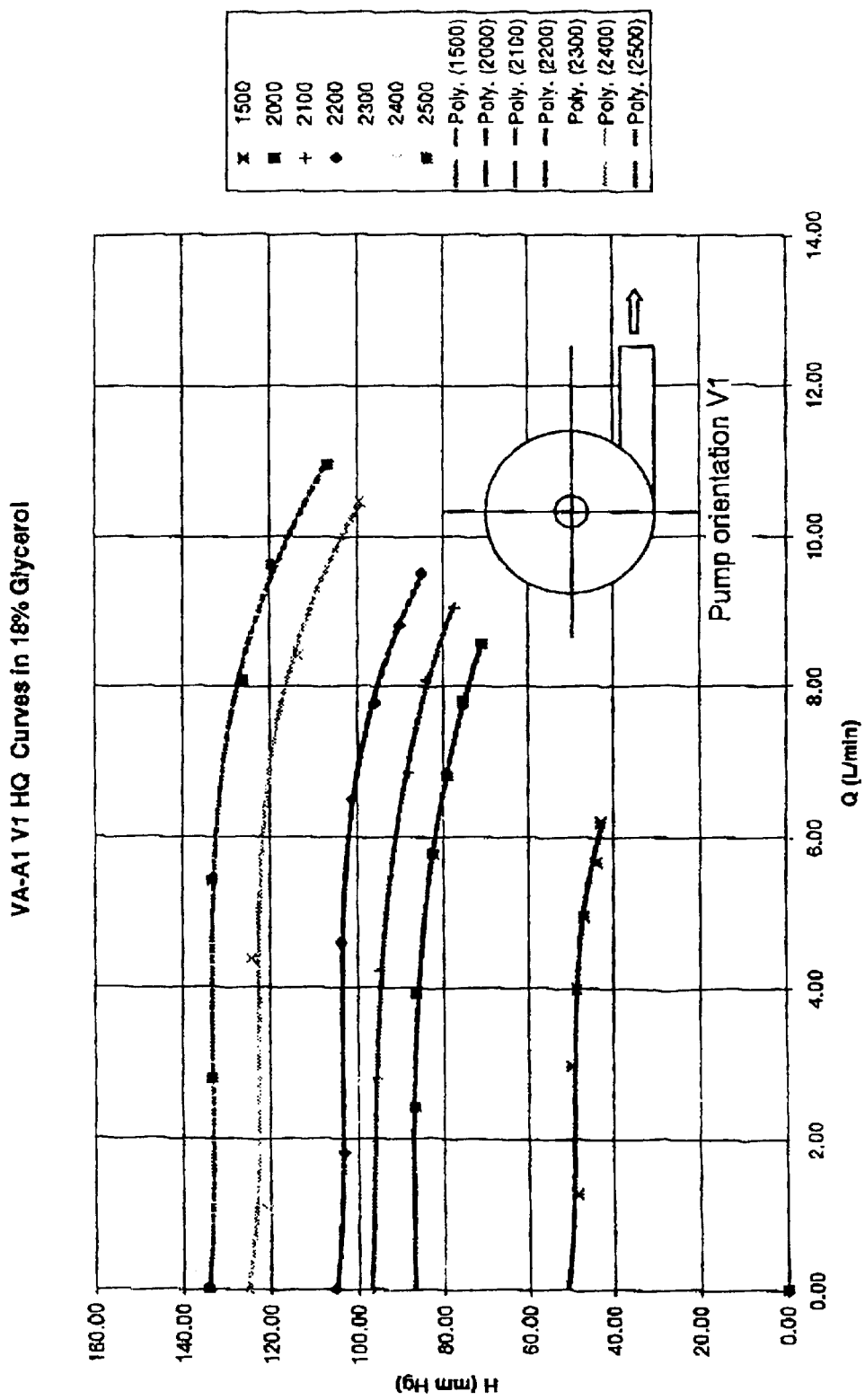
FIG. 13 is a graph of head versus flow for the pump assembly of FIG. 7.

FIG. 13 is a graph of pressure against flow for the pump assembly 200 where the fluid pumped is 18% glycerol for impeller rotation velocity over the range 1500 RPM to 2500 RPM. The 18% glycerol liquid is believed to be a good analogue for blood under certain circumstances.

Figure 14:
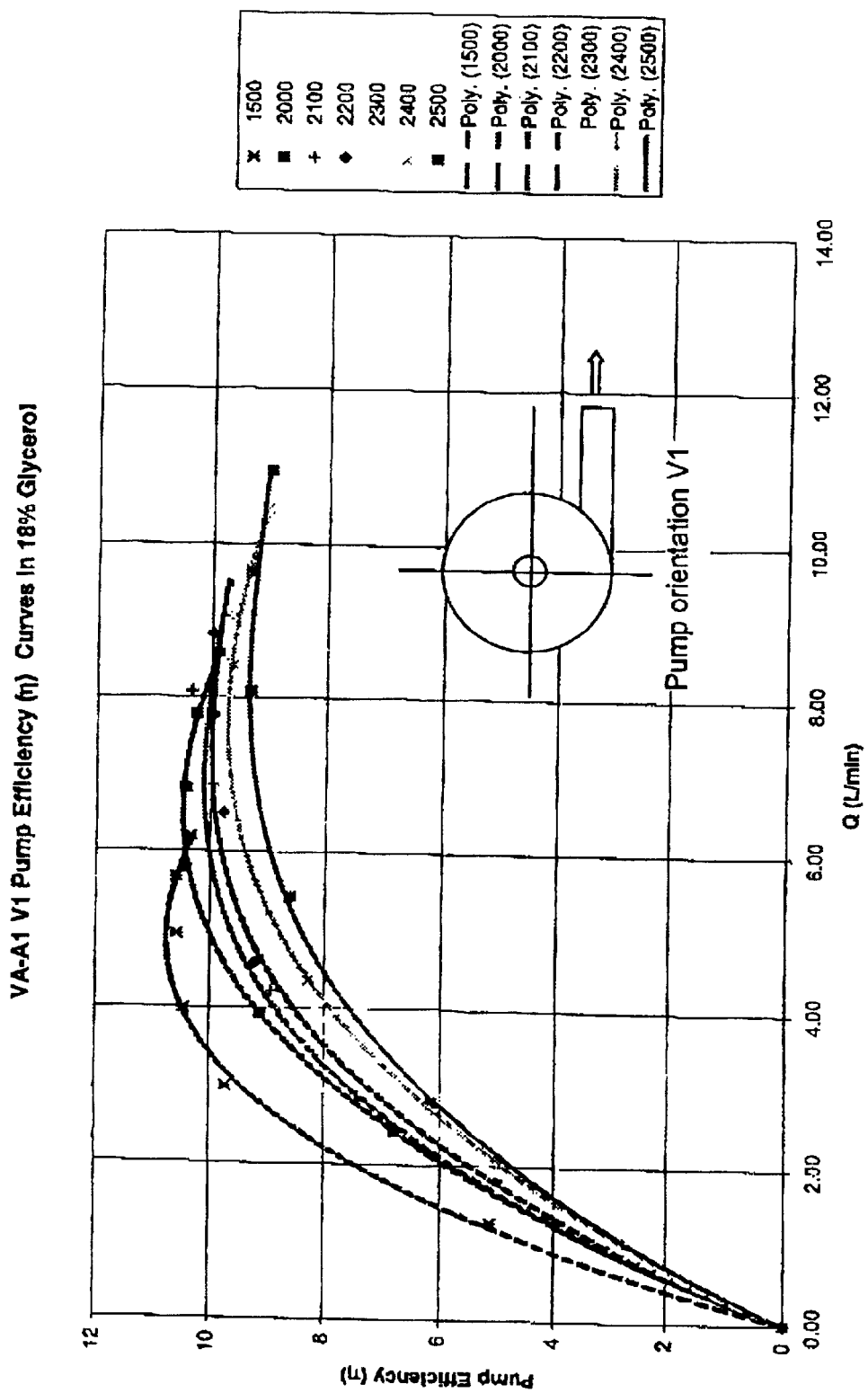
FIG. 14 is a graph of pump efficiency versus flow for the pump assembly of FIG. 7.

FIG. 14 graphs pump efficiency against flow for the same fluid over the same speed ranges as for FIG. 13.

Figure 15:
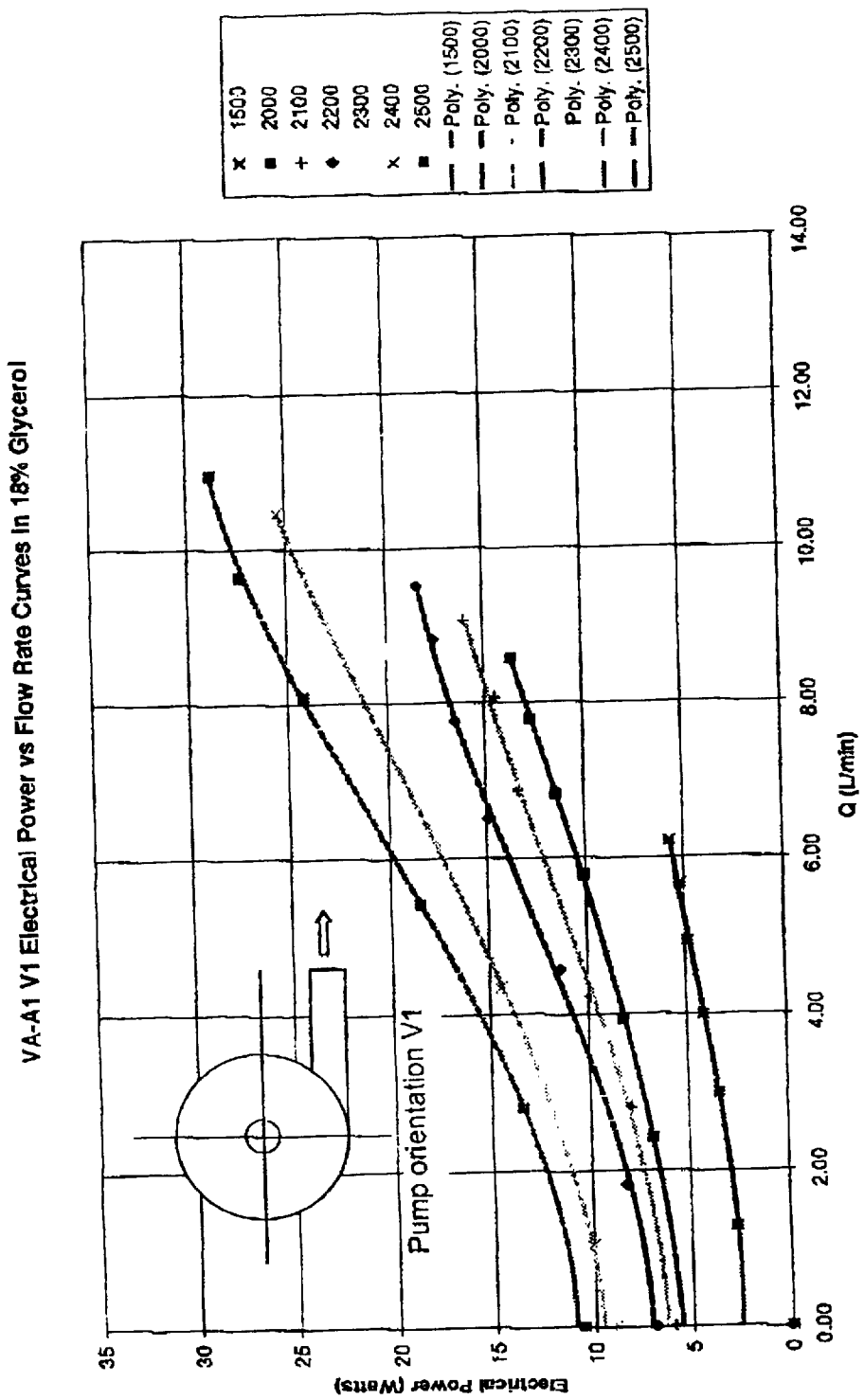
FIG. 15 is a graph of electrical power consumption versus flow for the pump assembly of FIG. 7.
Figure 16:
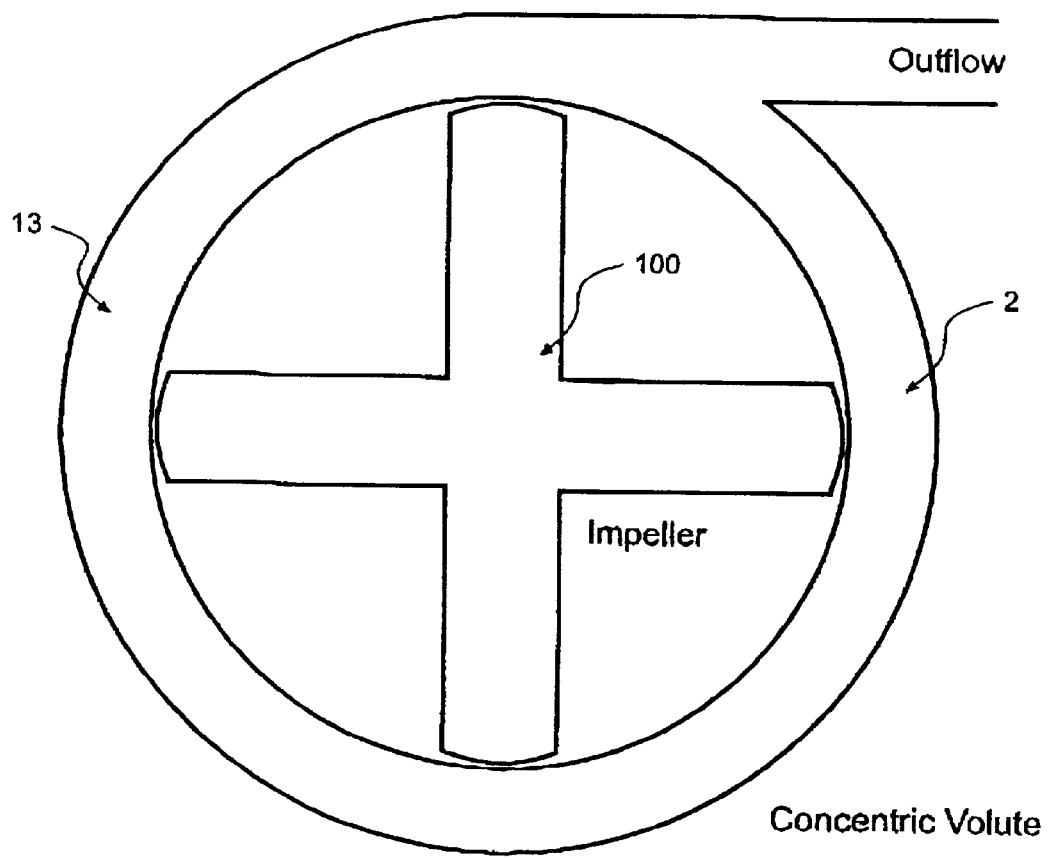
FIG. 16 is a plan, section view of the pump assembly showing a volute arrangement according to a preferred embodiment.

FIG. 15 is a graph of electrical power consumption against flow for the same fluid over the same speed ranges as for FIG. 13.

FURTHER EMBODIMENTS

The common theme running through the first, second and third embodiments described thus far is the inclusion in the impeller of a taper or other deformed surface which, in use, moves relative to the adjacent housing wall thereby to cause a restriction with respect to the line of movement of the taper or deformity thereby to generate thrust upon the impeller which includes a component substantially normal to the line of movement of the surface and also normal to the adjacent internal pump wall with respect to which the restriction is defined for fluid located therebetween.

In order to provide both radial and axial direction control at least one set of surfaces must be angled with respect to the longitudinal axis of the impeller (preferably at approximately 45° thereto) thereby to generate or resolve opposed radial forces and an axial force which can be balanced by a corresponding axial force generated by at least one other tapered or deformed surface located elsewhere on the impeller.

In the forms thus far described top surfaces of the blades 8, 207 are angled at approximately 450 with respect to the longitudinal axis of the impeller 100, 204 and arranged for rotation with respect to the internal walls of a similarly angled conical pump housing. The top surfaces are deformed so as to create the-necessary restriction in the gap between the top surfaces of the blades and the internal walls of the conical pump housing thereby to generate a thrust which can be resolved to both radial and axial components.

In the examples thus far the bottom faces of the blades 8, 207 comprise surfaces substantially lying in a plane at right angles to the axis of rotation of the impeller and, with their deformities define a gap with respect to a lower inside face of the pump housing against which a substantially only axial thrust is generated.

Other arrangements are possible which will also, relying on these principals, provide the necessary balanced radial and axial forces. Such arrangements can include a double cone arrangement where the conical top surface of the blades is mirrored in a corresponding bottom conical surface. The only concern with this arrangement is the increased depth of pump which can be a problem for in vivo applications where size minimisation is an important criteria.

Figure 18:
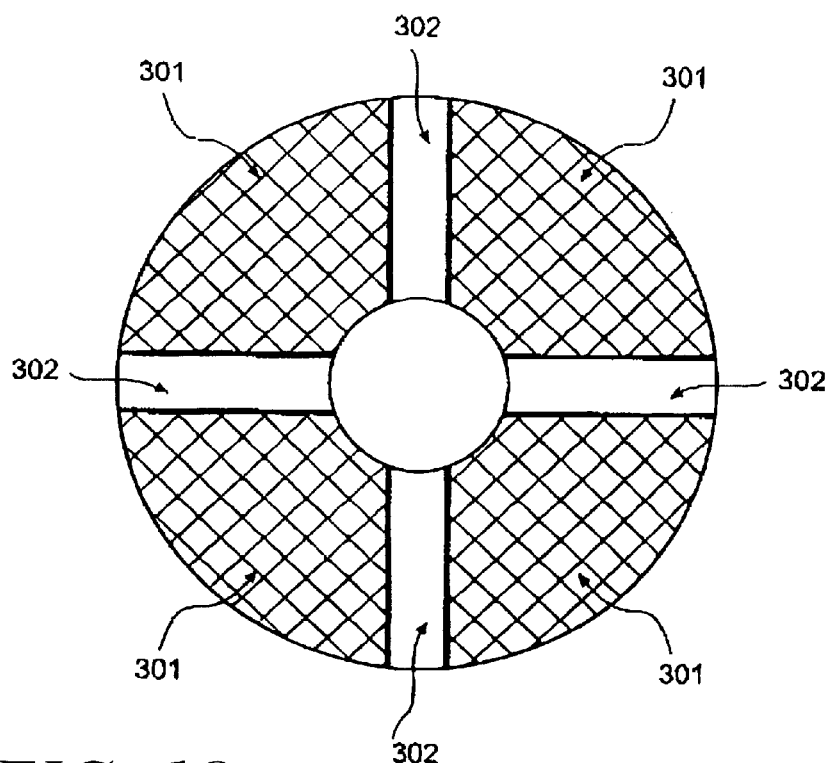
FIG. 18 is a plan view of an impeller according to a further embodiment of the invention.

With reference to FIG. 18 a further embodiment of the invention is illustrated comprising a plan view of the impeller 300 forming part of a "channel" pump. In this embodiment the blades 301 have been widened relative to the blades 207 of the third embodiment to the point where they are almost sector-shaped and the flow gaps between adjacent blades 301, as a result, take the form of a channel 302, all in communication with axial cavity 303.

Figure 19:
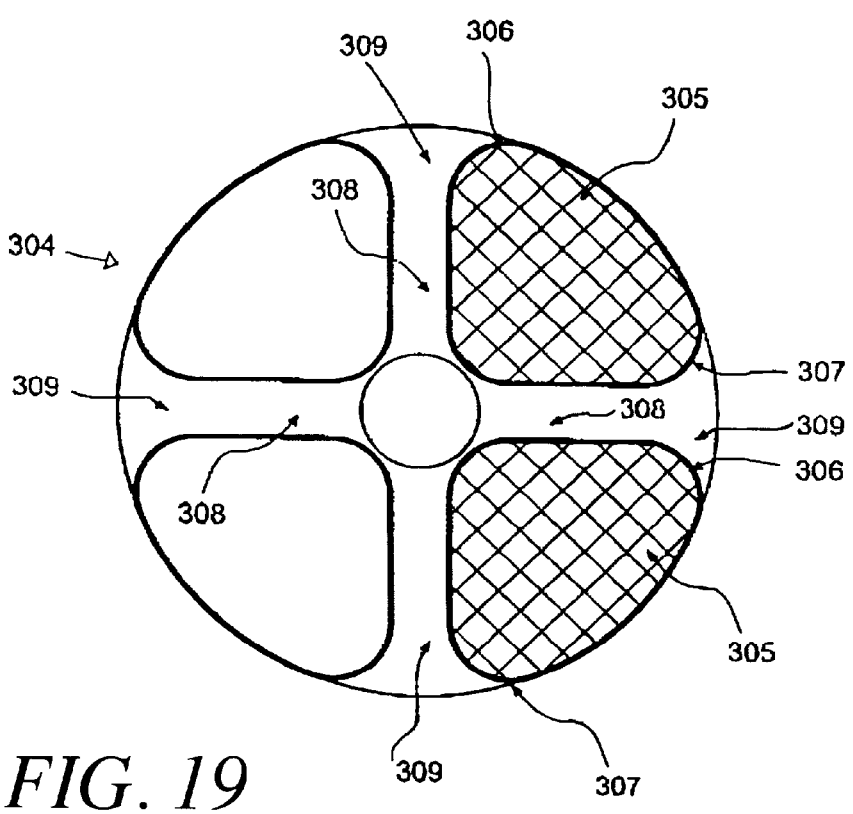
FIG. 19 is a plan view of an impeller according to a further embodiment of the invention.

A further modification of this arrangement is illustrated in FIG. 19 wherein impeller 304 includes sector-shaped blades 305 having curved leading and trailing portions 306, 307 respectively thereby defining channels 308 having fluted exit portions 309.

As with the first and second embodiments the radial and axial hydrodynamic forces are generated by appropriate profiling of the top and bottom faces of the blades 301, 305 (not shown in FIGS. 18 and 19).

Figure 20:
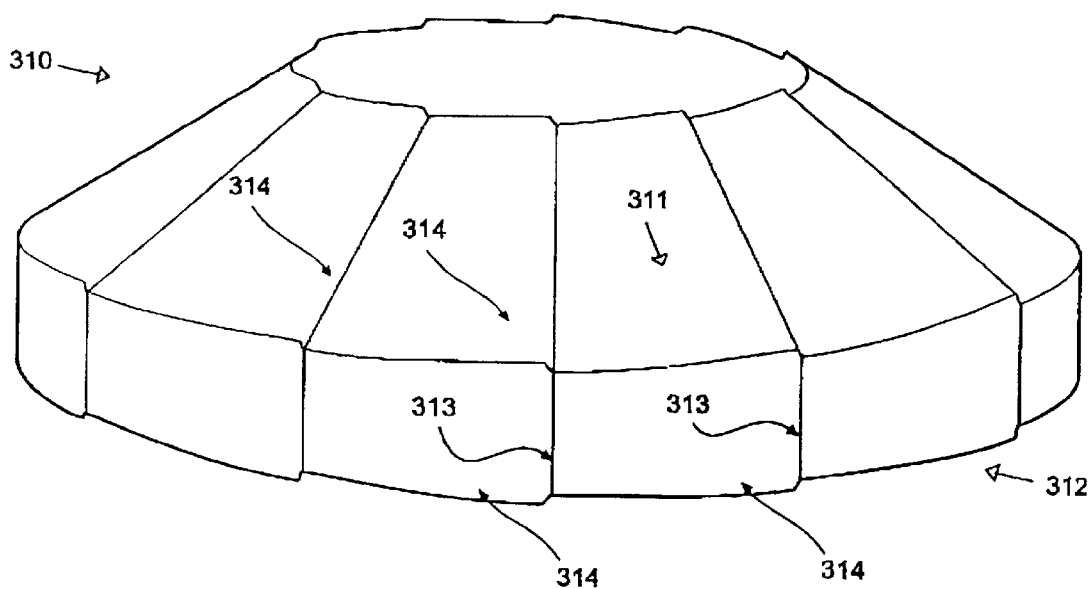
FIG. 20 is a perspective view of an impeller according to a further embodiment of the invention.

A further embodiment of a pump assembly according to the invention comprises an impeller 310 as illustrated in FIG. 20 where, conceptually, the upper and lower surfaces of the blades of previous embodiments are interconnected by a top shroud 311 and a bottom shroud 312. In this embodiment the blades 313 can be reduced to a very small width as the hydrodynamic behaviour imparted by their surfaces in previous embodiments is now given effect by the profiling of the shrouds 311, 312 which, in this instance, comprises a series of smooth-edged wedges with the leading surface of one wedge directly interconnected to the trailing edge of the next leading wedge 314.

As for previous embodiments the top shroud 311 is of overall conical shape thereby to impart both radial and axial thrust forces whilst the bottom shroud 312 is substantially planar thereby to impart substantially only axial thrust forces.

The foregoing describes the principles of the present invention, and modifications, obvious to those skilled in the art, can be made thereto without departing from the scope of the invention.

INDUSTRIAL APPLICABILITY

The pump assembly 1, 200 is applicable to pump fluids such as blood on a continuous basis. With its expected reliability it is particularly applicable as an in vivo heart assist pump.

The pump assembly can also be used with advantage for the pumping of other fluids where damage to the fluid due to high shear stresses must be avoided or where leakage of the fluid must be prevented with a very high degree of reliability—for example where the fluid is a dangerous fluid.

What is claimed is:

1. A rotary blood pump having an impeller suspended solely hydrodynamically within a pump housing by thrust forces generated by the impeller during movement in use of the impeller as it rotates about an impeller axis, and wherein said thrust forces are generated by edges of said blades of said impeller; and wherein said edges of said blades are shaped such that a gap between distal edges of each blade and the adjacent pump housing at the leading edge of the blade is greater than at the trailing edge so that the fluid which is drawn through the gap experiences a wedge shaped restriction which generates a thrust.

2. The blood pump of claim 1, wherein said edges of said blades are tapered or non-planar, so that a thrust is created between the edges and the pump housing during relative movement therebetween.

3. The blood pump of claim 1, wherein the pump is of centrifugal type or mixed flow type with blades of said impeller open on both front and back faces of the pump housing.

4. The blood pump of claim 3, wherein the front face of the pump housing is made conical, in order that the thrust force perpendicular to the conical surface has a radial component, which provides a radial restoring force to a radial displacement of the impeller axis during use.

5. The blood pump of claim 1, wherein the driving torque of said impeller derives from the magnetic interaction between permanent magnets within the blades of the impeller and oscillating currents in windings encapsulated in the pump housing.

6. The rotary blood pump of claim 5, wherein said pump is of axial type.

7. The rotary blood pump of claim 6, wherein within a uniform cylindrical section of the pump housing, said impeller includes tapered blade edges which form a radial hydrodynamic bearing.

8. The rotary blood pump of claim 7, wherein an interior of the pump housing is made with reducing radius at the two ends, and wherein the end hydrodynamic thrust forces have an axial component which can provide the axial bearing.

9. The rotary blood pump of claim 7, wherein magnetic forces provide the axial bearing.

10. The pump of claim 1, wherein said impeller includes magnetic material therein, the magnetic material being encapsulated within a biocompatible shell or coating.

11. The pump of claim 10, wherein said biocompatible shell or coating comprises a material which can be applied at low temperature, such as a diamond coating.

12. The pump of claim 1, wherein internal walls of said pump which can come into contact with said blades during use are coated with titanium nitride or diamond coating.

13. A seal-less, shaft-less pump comprising a housing defining a chamber therein and having a liquid inlet to said chamber and a liquid outlet from said chamber; said pump further including an impeller located within said chamber;

the arrangement between said impeller, said inlet, said outlet and the internal walls of said chamber being such that upon rotation of said impeller about an impeller axis relative to said housing, liquid is urged from said inlet through said chamber to said outlet, and wherein thrust forces are generated by said impeller; and wherein said thrust forces are generated by edges of blades of said impeller, and wherein said edges of said blades are shaped such that a gap is formed between an end of each blade and the adjacent housing and the gap at a leading edge of each of said blades is greater than at a trailing edge thereof whereby fluid which is drawn through the gap experiences a wedge shaped restriction which generates a thrust relative to said housing.

14. The pump of claim 13, wherein said edges of said blades are tapered or non-planar.

15. The pump of claim 13, wherein the pump is of centrifugal type or mixed flow type with said blades of said impeller open on both front and back faces of the pump housing.

16. The pump of claim 15, wherein the front face of the pumphousing is conical, in order that the thrust perpendicular to its conical surface at any point has a radial component, which provides a radial restoring force to a radial displacement of the impeller axis.

17. The pump of claim 13, wherein the driving torque of said impeller derives from the magnetic interaction between permanent magnets within the blades of the impeller and oscillating currents in windings encapsulated in the pump housing.

18. The pump of claim 13, wherein said pump is of axial type.

19. The pump of claim 18, wherein within a uniform cylindrical section of the pump housing, tapered blade edges form a radial hydrodynamic bearing.

20. The pump of claim 18, wherein the pump housing is made with reducing radius at opposed ends, and wherein the end hydrodynamic thrust forces have an axial component which can provide an axial bearing.

21. The pump of claim 18, wherein magnetic forces provide an axial bearing.

22. The pump of claim 13, wherein said impeller includes magnetic material therein, the magnetic material encapsulated within a biocompatible shell or coating.

23. The pump of claim 22, wherein said biocompatible shell or coating comprises a diamond coating.

24. The pump of claim 22, wherein internal walls of said pump which can come into contact with said impeller during use are coated with titanium nitride or diamond coating.

25. The pump of claim 13, wherein at least upper and lower surfaces of said blades of said impeller are interconnected by a structure having deformities in the outer surfaces thereof so that a thrust is created between said surfaces and the adjacent pump casing during relative movement therebetween.

26. A method of hydrodynamically suspending an impeller within a rotary pump for support in at least one of a radial or axial direction, said method comprising incorporating a deformed surface in at least part of said impeller so that, in use, a thrust is created between said deformed surface and the adjacent pump casing during relative movement therebetween; and wherein said deformed surface includes a taper; wherein said taper is arranged so that there is a gap between a distal end of each blade of said impeller and the adjacent housing, and a larger gap at a leading edge thereof between said impeller and said pump casing than at a trailing edge thereof.

* * * * *

UNITED STATES PATENT AND TRADEMARK OFFICE
CERTIFICATE OF CORRECTION

PATENT NO. : 6,227,797 B1  
DATED : May 8, 2001  
INVENTOR(S) : Watterson et al.

It is certified that error appears in the above-identified patent and that said Letters Patent is hereby corrected as shown below:

<u>Title page,</u>  
Replace "Continuation of application No. PCT/AU98/00725, filed on Sep. 18, 1998" with -- Continuation of application No. PCT/AU98/00725, filed on Sep. 7, 1998 --.

Signed and Sealed this

Fifth Day of November, 2002

Attest:

Attesting Officer

JAMES E. ROGAN  
*Director of the United States Patent and Trademark Office*

UNITED STATES PATENT AND TRADEMARK OFFICE
CERTIFICATE OF CORRECTION

PATENT NO.    : 6,227,797 B1
DATED         : May 8, 2001
INVENTOR(S)   : Watterson et al.

It is certified that error appears in the above-identified patent and that said Letters Patent is hereby corrected as shown below:

<u>Title page,</u>
Item [73], Assignee, should read -- Ventrassist Pty. Ltd., Labrador, Queensland, Australia and University of Technology Sydney, New South Wales, Australia --
Add Item:
-- [30]  Foreign Application Priority Data
Sept. 5, 1997 (AU)..........................PO 9027 --

Signed and Sealed this

Twenty-ninth Day of July, 2003

JAMES E. ROGAN
*Director of the United States Patent and Trademark Office*